United States Patent [19]
Yoon

[11] Patent Number: 6,059,734
[45] Date of Patent: May 9, 2000

[54] METHODS OF COLLECTING TISSUE AT OBSTRUCTED ANATOMICAL SITES

[76] Inventor: InBae Yoon, 2101 Highland Ridge Dr., Phoenix, Md. 21131

[21] Appl. No.: 09/071,809

[22] Filed: May 5, 1998

Related U.S. Application Data

[63] Continuation-in-part of application No. 08/369,545, Jan. 6, 1995.
[60] Provisional application No. 60/050,092, Jun. 18, 1997.

[51] Int. Cl.⁷ .................................................. A61B 5/00
[52] U.S. Cl. ............................................................. 600/565
[58] Field of Search ........................... 600/104, 153, 600/160, 562, 564–567

[56] References Cited

U.S. PATENT DOCUMENTS

| | | |
|---|---|---|
| 716,040 | 12/1902 | Holt . |
| 1,909,967 | 5/1933 | Jones . |
| 3,039,468 | 6/1962 | Price . |
| 3,253,594 | 5/1966 | Matthews et al. . |
| 3,459,175 | 8/1969 | Miller . |
| 3,495,586 | 2/1970 | Regenbogen . |
| 3,512,528 | 5/1970 | Whitehead et al. . |
| 3,557,794 | 1/1971 | VanPatten . |
| 3,598,119 | 8/1971 | White . |
| 3,635,223 | 1/1972 | Klieman . |
| 3,833,003 | 9/1974 | Taricco . |
| 3,882,852 | 5/1975 | Sinnreich . |
| 3,890,970 | 6/1975 | Gullen . |
| 3,952,742 | 4/1976 | Taylor . |
| 4,019,499 | 4/1977 | Fitzgerald . |
| 4,043,338 | 8/1977 | Homm et al. . |
| 4,077,412 | 3/1978 | Moossun . |
| 4,089,337 | 5/1978 | Kronner . |
| 4,219,026 | 8/1980 | Layton . |
| 4,291,687 | 9/1981 | Sinnreich . |
| 4,372,295 | 2/1983 | Heckele . |
| 4,430,076 | 2/1984 | Harris . |
| 4,535,772 | 8/1985 | Yoon . |
| 4,568,326 | 2/1986 | Rangaswamy . |
| 4,575,371 | 3/1986 | Nordgvist et al. . |

(List continued on next page.)

FOREIGN PATENT DOCUMENTS

| | | |
|---|---|---|
| 0 432 363 | 2/1991 | European Pat. Off. . |
| 3 519 626 | 12/1986 | Germany . |

OTHER PUBLICATIONS

"Soft–Wand, Atraumatic Tissue Manipulation Balloon," Cabot Medical, 2021 Cabot Boulevard West, Langhorne, PA 19047 USA.
"Expose Retractor, Inflatable Retractor," Advanced Surgical, Inc., 305 College Road East, Princeton, New Jersey 08540, Patent No. 5,308,327.
"Expose Retractor, Reusable Retract," Advanced Surgical, Inc., 305 College Road East, Princeton, New Jersey 08540, Patent Pending PN70046.
"A Conservative Approach to Laparoscopic Hernia Repair", Origin Medsystems, Inc., 135Constitution Drive, Menlo Park, CA 94025 USA.
"Delivering the Future First in Bladder Neck Suspension Surgery", Origin Medsystems, Inc. 135 Constitution Drive, Menlo Park, CA 94025 USA.
"New Directions in Laparoscopy", Origin Medsystems, Inc., 135 Constitution Drive, Menlo Park, CA 94025 USA.

*Primary Examiner*—Max Hindenburg
*Attorney, Agent, or Firm*—Blank Rome Comisky & McCauley LLP

[57] ABSTRACT

A method of collecting a tissue portion at an obstructed site within anatomical tissue comprising the steps of inserting a distal end of a guide member in the anatomical tissue to position the distal end of the guide member at an obstructed site adjacent a tissue portion to be collected, visualizing the obstructed site remotely with an endoscope, injecting a viscous, optically clear fluidic material through the guide member for release at the obstructed site to displace the anatomical tissue and create a fluid filled space in the anatomical tissue adjacent the tissue portion, introducing a distal end of a tissue collector in the space, dissecting the tissue portion from the anatomical tissue with the distal end of the tissue collector and removing the tissue portion from the anatomical tissue.

33 Claims, 19 Drawing Sheets

U.S. PATENT DOCUMENTS

| | | |
|---|---|---|
| 4,607,619 | 8/1986 | Seike et al. . |
| 4,608,965 | 9/1986 | Anspach, Jr. et al. . |
| 4,651,753 | 3/1987 | Lifton ................................ 128/751 |
| 4,748,982 | 6/1988 | Horzewski et al. . |
| 4,775,362 | 10/1988 | Kronner . |
| 4,931,059 | 6/1990 | Markham ............................ 606/185 |
| 4,966,162 | 10/1990 | Wang ................................. 128/750 |
| 4,966,583 | 10/1990 | Debbas . |
| 4,998,527 | 3/1991 | Meyer . |
| 5,002,557 | 3/1991 | Hasson . |
| 5,002,558 | 3/1991 | Klein et al. . |
| 5,007,898 | 4/1991 | Rosenbluth et al. . |
| 5,041,093 | 8/1991 | Chu . |
| 5,074,871 | 12/1991 | Groshong . |
| 5,090,419 | 2/1992 | Palestrant ............................ 128/754 |
| 5,103,804 | 4/1992 | Abele et al. . |
| 5,113,846 | 5/1992 | Hiltebrandt et al. . |
| 5,163,949 | 11/1992 | Bonutti . |
| 5,176,128 | 1/1993 | Andrese . |
| 5,178,133 | 1/1993 | Pena . |
| 5,183,463 | 2/1993 | Debbas ................................ 604/98 |
| 5,183,464 | 2/1993 | Dubrul et al. . |
| 5,188,630 | 2/1993 | Christoudias . |
| 5,195,507 | 3/1993 | Bilweis . |
| 5,195,533 | 3/1993 | Chin et al. ........................... 128/754 |
| 5,197,948 | 3/1993 | Ghodsian . |
| 5,246,421 | 9/1993 | Saab . |
| 5,256,139 | 10/1993 | Ghodsian . |
| 5,269,753 | 12/1993 | Wilk . |
| 5,273,026 | 12/1993 | Wilk . |
| 5,275,610 | 1/1994 | Eberbach . |
| 5,295,952 | 3/1994 | Pietrafitta . |
| 5,301,682 | 4/1994 | Debbas . |
| 5,308,327 | 5/1994 | Heaven et al. . |
| 5,318,586 | 6/1994 | Ereren . |
| 5,320,604 | 6/1994 | Walker et al. . |
| 5,320,605 | 6/1994 | Sahota . |
| 5,331,947 | 7/1994 | Shturman . |
| 5,345,927 | 9/1994 | Bonutti . |
| 5,353,804 | 10/1994 | Kornberg et al. ..................... 128/754 |
| 5,354,270 | 10/1994 | Wilk et al. . |
| 5,354,356 | 10/1994 | Hofling . |
| 5,359,995 | 11/1994 | Sewell, Jr. . |
| 5,400,770 | 3/1995 | Nakao et al. . |
| 5,405,360 | 4/1995 | Tovey . |
| 5,445,645 | 8/1995 | Debbas ............................... 606/192 |
| 5,562,640 | 10/1996 | McCabe et al. ...................... 604/280 |
| 5,605,537 | 2/1997 | Ivey ................................... 604/21 |
| 5,662,674 | 9/1997 | Debbas ............................... 606/192 |
| 5,683,413 | 11/1997 | Miyagi ............................... 606/205 |
| 5,715,832 | 2/1998 | Koblish et al. ...................... 128/754 |
| 5,718,237 | 2/1998 | Haaga ................................ 128/751 |

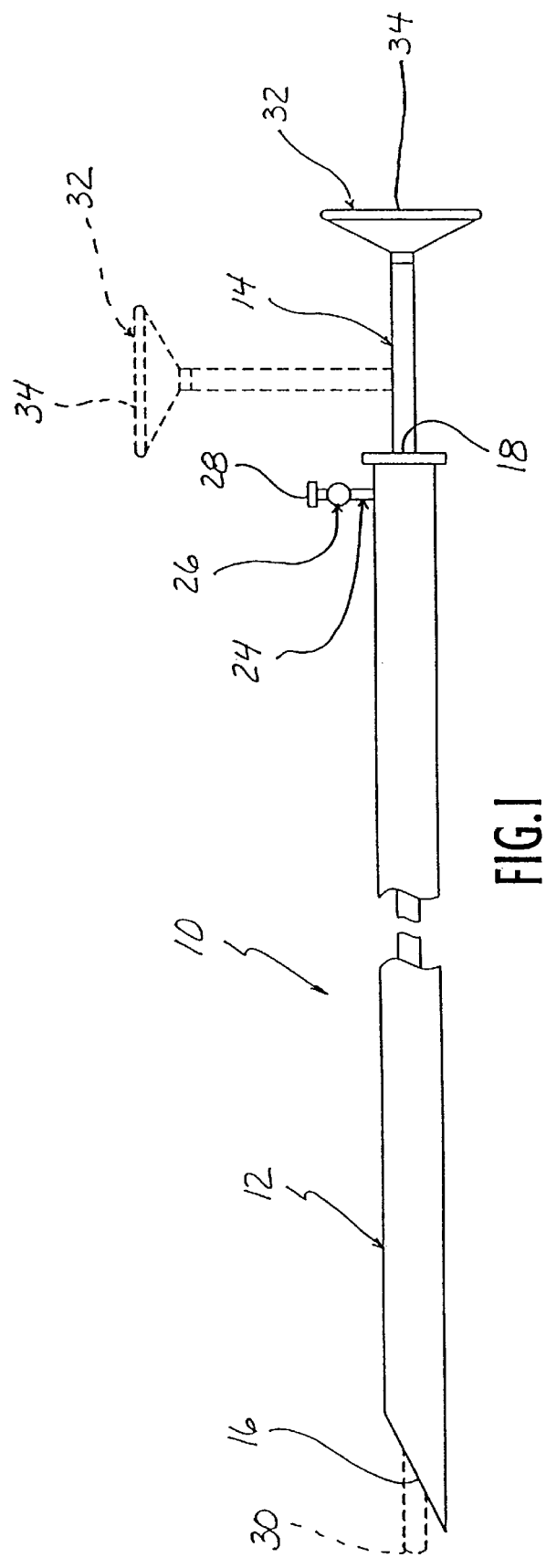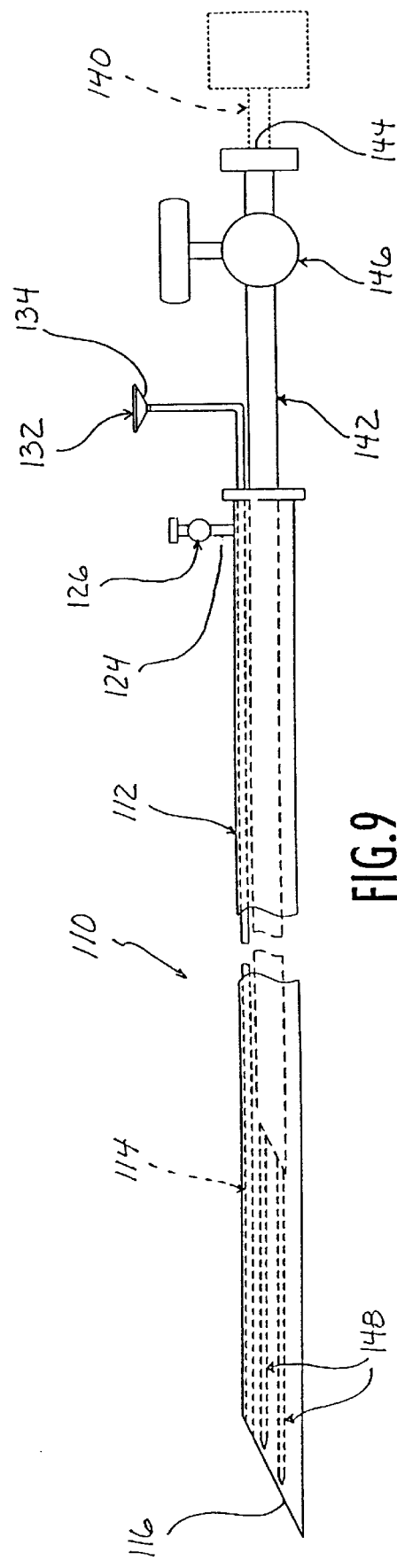

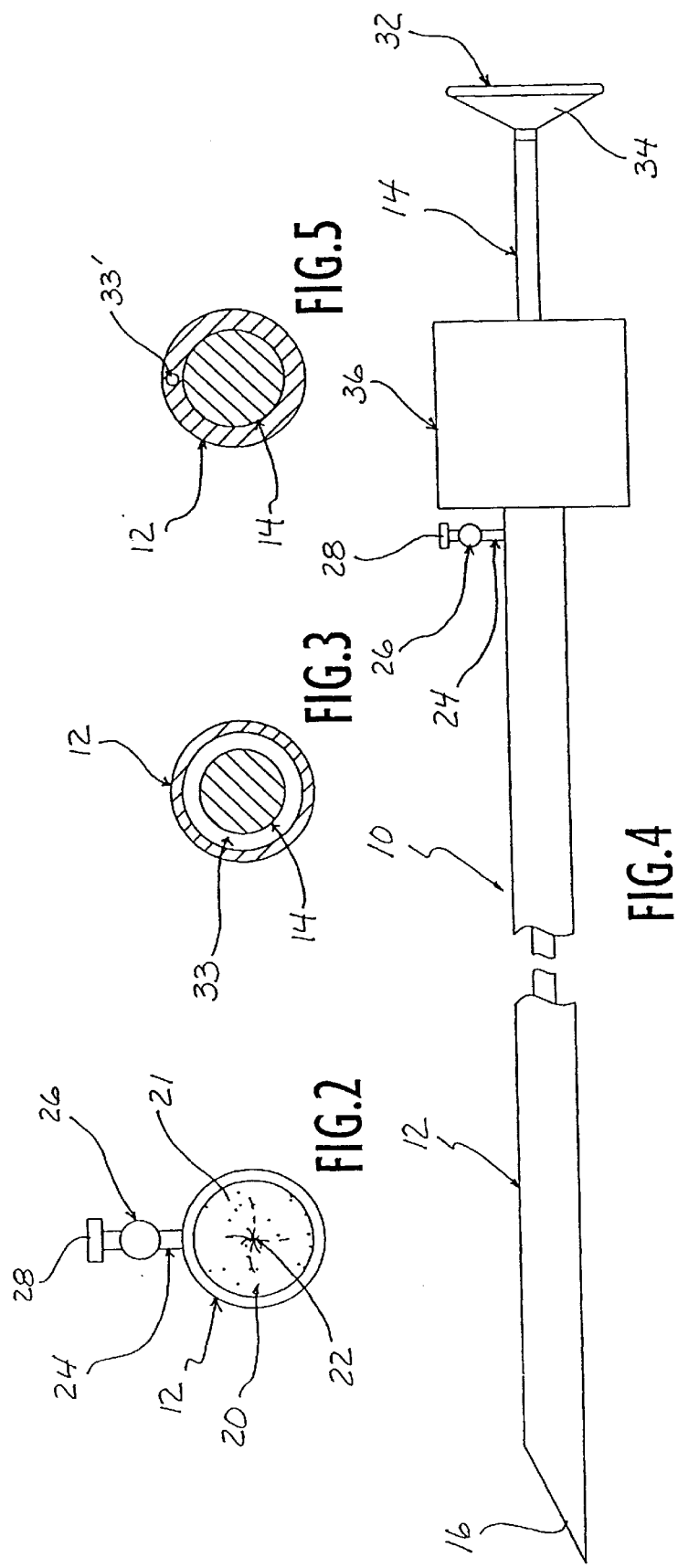

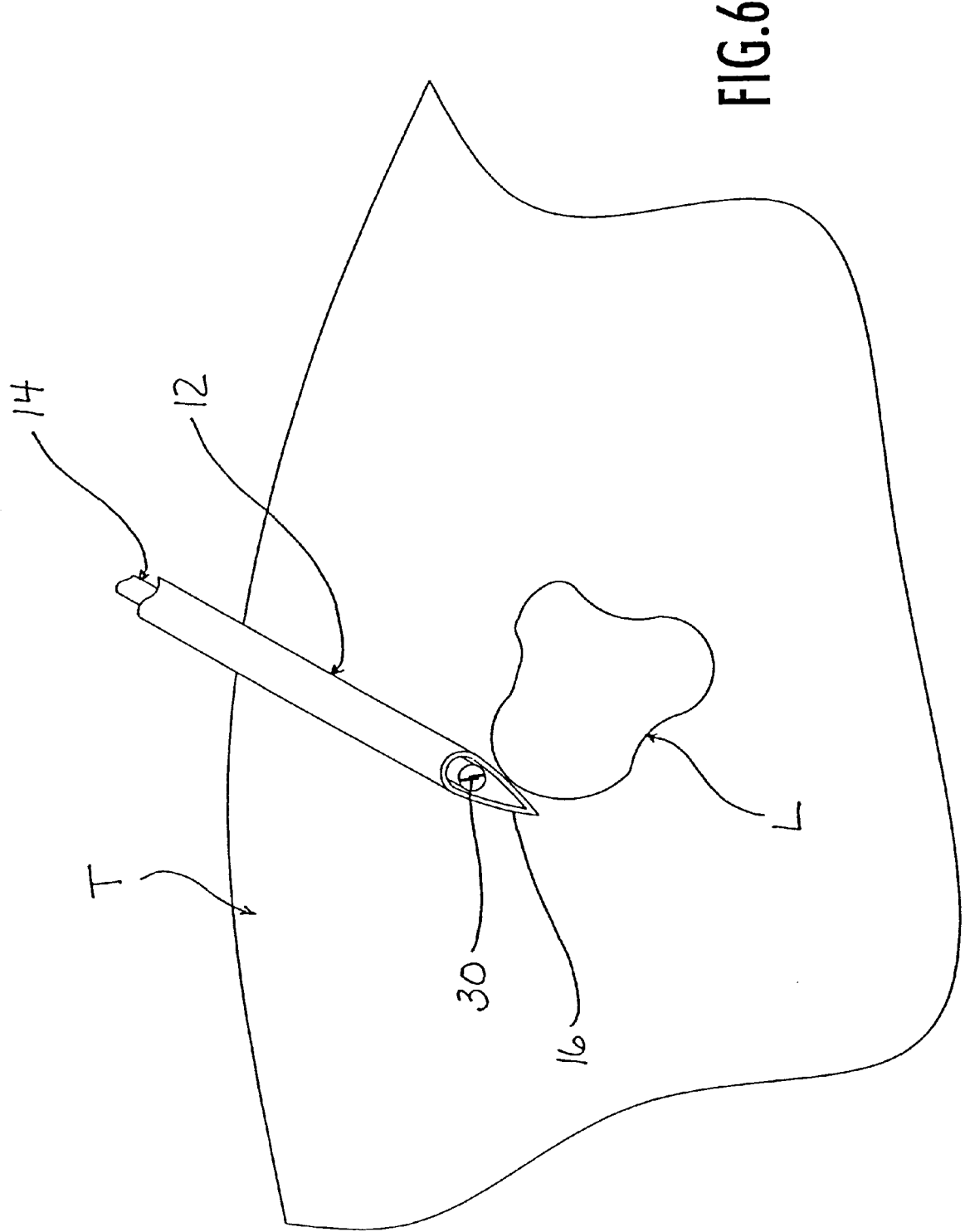

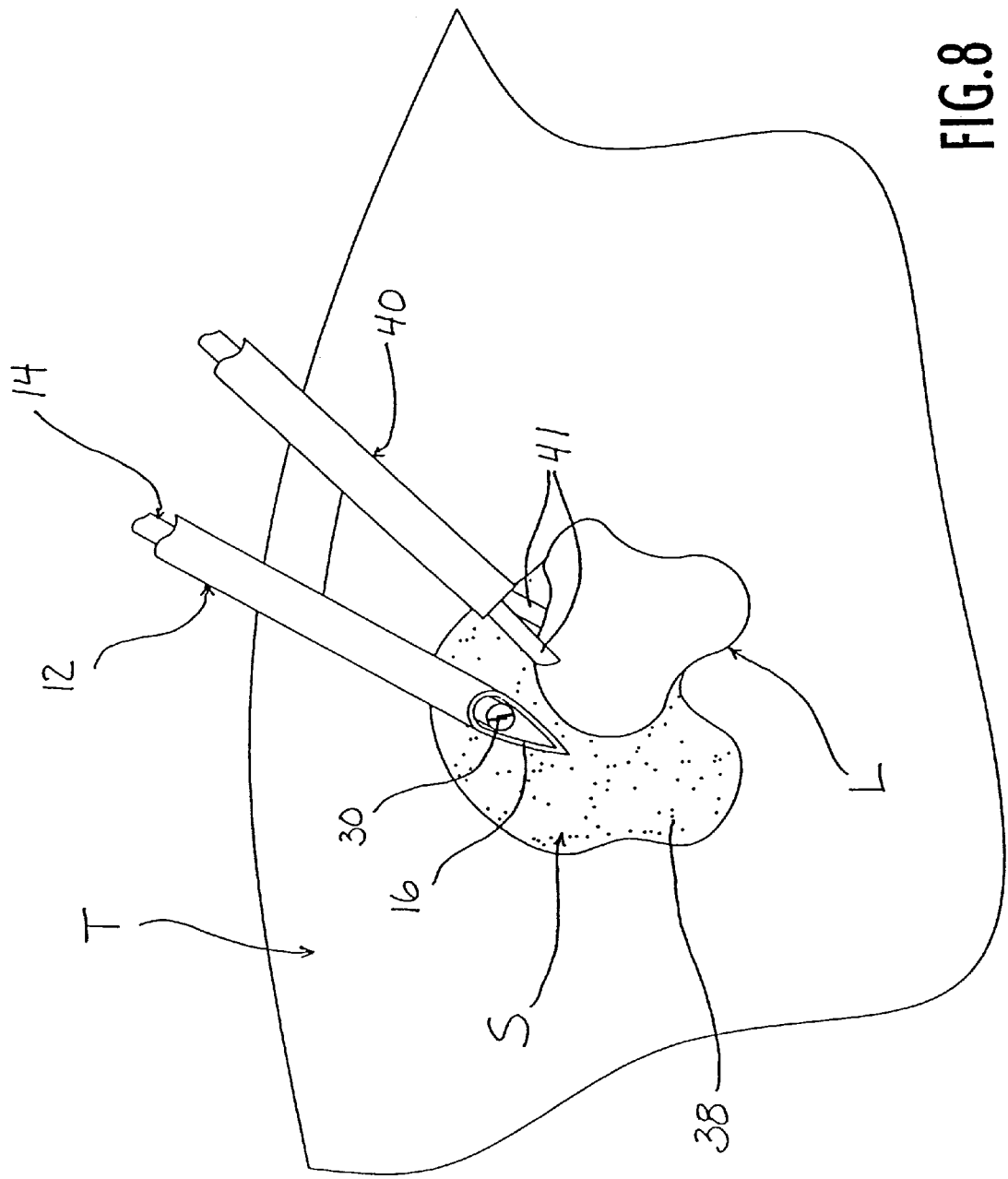

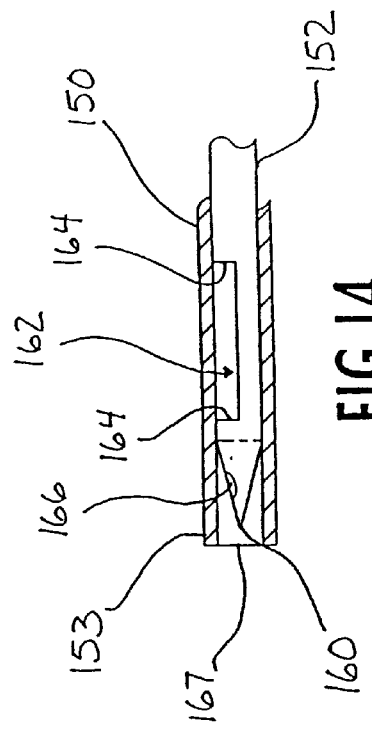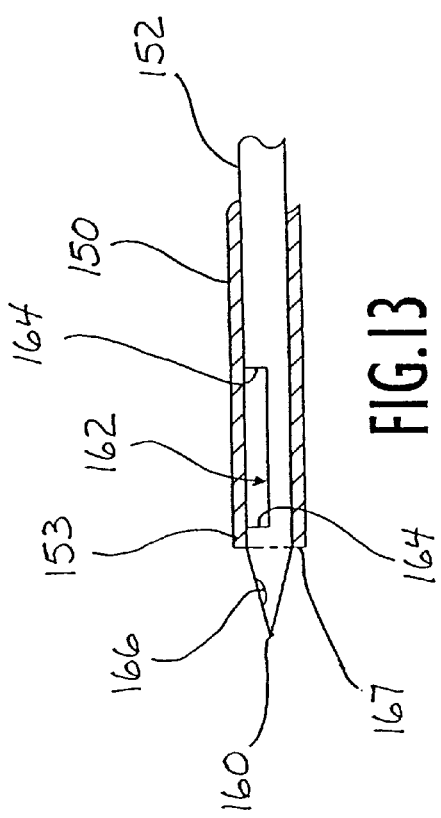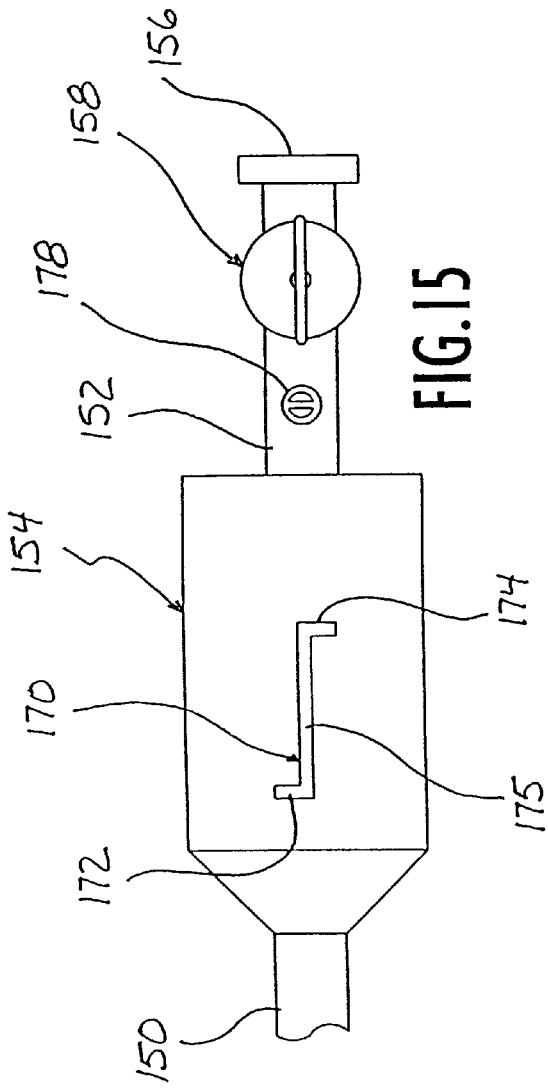

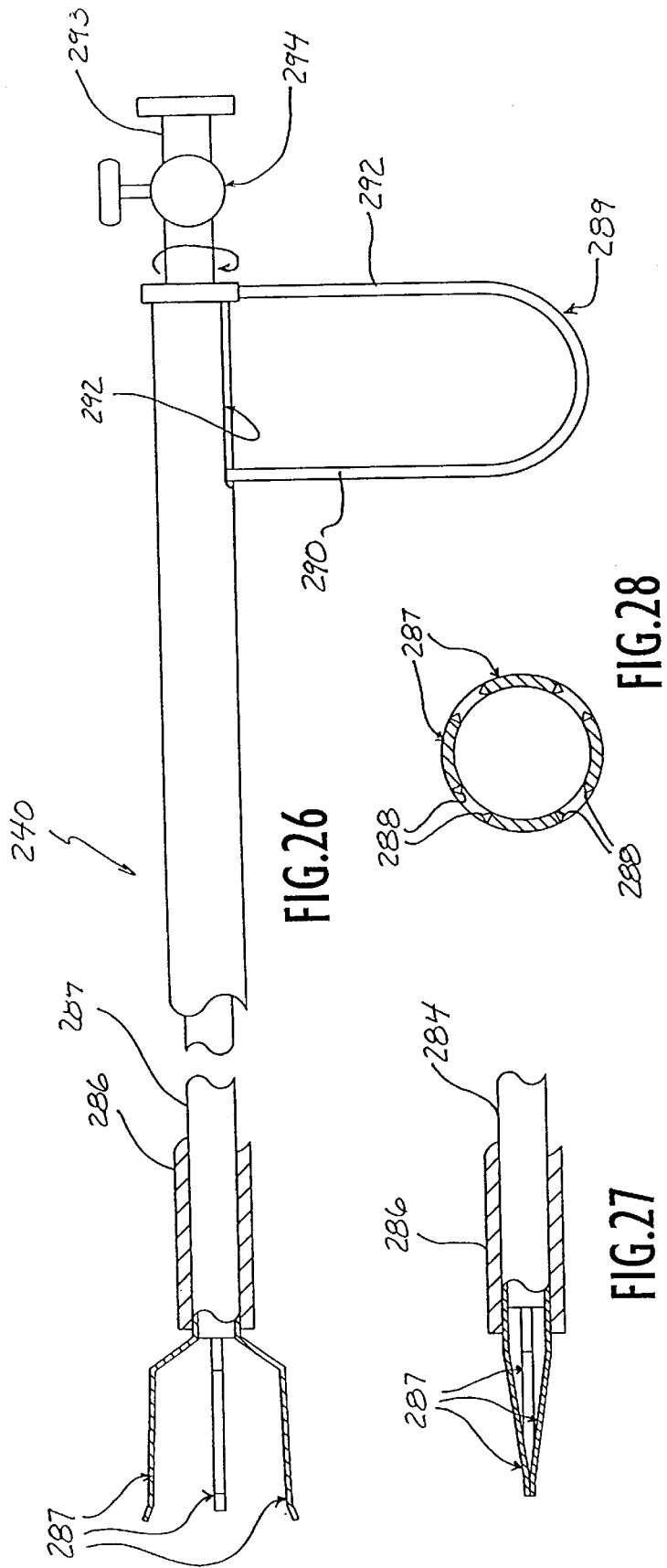

METHODS OF COLLECTING TISSUE AT OBSTRUCTED ANATOMICAL SITES

CROSS-REFERENCE TO RELATED PATENT APPLICATIONS

This application is a continuation-in-part of pending prior application Ser. No. 08/369,545, filed Jan. 6, 1995. This application is related to prior provisional application Ser. No. 60/050,092, filed Jun. 18, 1997. The disclosures of the foregoing patent applications are incorporated herein by reference.

BACKGROUND OF THE INVENTION

1. Field of the Invention

The present invention pertains to minimally invasive surgical procedures and, more particularly, to minimally invasive procedures for collecting tissue at obstructed anatomical sites.

2. Discussion of the Related Art

Endoscopic or minimally invasive surgical procedures have become well accepted due to the reduced trauma and recovery time for the patient as well as the associated decrease in hospitalization time and cost. It is desirable to expand the types of procedures that can be performed using minimally invasive techniques; however, for such procedures to be universally accepted, the procedures must be capable of being performed in, at most, the same time required for the same procedure performed by open surgery and must be capable of being performed by surgeons of varying degrees of skill.

There are many areas of surgery to which it would be desirable to extend minimally invasive techniques, and one such area is the treatment of tissue disposed at portions of the anatomy other than portions, such as anatomical cavities, providing sufficient space to perform procedures. The terms "tissue" and "organ structure" are used herein synonymously and include portions or the entireties of all anatomical parts including malignant and benign growths and tumors. Examples of such areas of treatment include, for example, preperitoneal hernia repair, bladder neck suspension, separation or dissection of connected or adhering tissue and excision or biopsy of masses or tumors within anatomical parts such as the breast or the brain, and the like. When procedures are performed in cavities such as the abdomen and thorax, conventional retractors or other tissue manipulators can normally be used for exposure of tissue to be treated; however, where the tissue to be treated is located in obstructed anatomical sites such as in very small cavities, in potential cavities such as between layers of anatomical walls, in non-layered or homogeneous tissue or in a single layer of tissue, visualization of the operative site is obstructed as well as is space for maneuvering instruments making minimally invasive surgery extremely difficult to perform in an acceptable manner. As used herein, the term "obstructed site" refers to anatomical spaces or cavities of such a small size that procedures cannot be visualized and/or performed as well as anatomical locations where no space or cavity exists. In the latter case, the obstructed site includes "potential spaces or cavities", such as between layers of anatomical wall that can be separated or spaced such as the peritoneum, fascia and muscles of the abdominal wall and the epidural spaces between the dura matter and the brain and spinal cord, between tissue structure that is normally connected, adhering, closed or collapsed and locations within homogenous tissue that is not separable on a layer-by-layer or constituent basis such as the breast, the brain and the lung.

Tumors or other abnormal, atypical or suspicious growths or changes in anatomical tissue generally must be biopsied to determine whether the growths or changes are benign or malignant. Where a growth is malignant, it is desirable to remove the growth to prevent malignant or cancerous cells from metastasizing or spreading to other portions of the patient's body. However, certain benign growths need not be removed and can merely be monitored. Accordingly, it is common to collect or obtain a tissue specimen of an abnormal or atypical growth or changed area to determine the characteristics of the growth or changed area and the optimum protocol for dealing with the growth or changed area. The procedure of collecting and analyzing a tissue specimen is known as "biopsy".

In the area of breast biopsy, traditional biopsy methods involve making an incision in the breast tissue to collect a tissue specimen in an open surgical procedure. However, this often requires general anesthesia and leaves a significant scar. Endoscopic or minimally invasive surgical procedures are preferred for obtaining specimens of growths due to the reduced trauma and recovery time for the patient as well as the decreased hospitalization time and costs associated with such procedures. One minimally invasive procedure, known as "needle biopsy", uses a needle inserted through soft tissue and into a tumor or the like to remove a specimen of the tumor. However, a specimen obtained through conventional needle biopsy procedures is ordinarily small. Also, without a reliable device to dissect or cut the specimen, other than the needle itself, the needle often has to be inserted into the anatomical tissue several times before an adequate specimen is collected. Further, due to the small size of needle biopsy specimens, the nature of the abnormality is often misdiagnosed, resulting in unnecessary surgery to remove the abnormality or the failure to remove a dangerous, malignant abnormality.

When a growth is diagnosed as being malignant or otherwise dangerous, the growth is often removed surgically. Conventionally, this is accomplished by open surgical techniques in which the tumor and surrounding tissue are dissected and removed through a relatively large incision. The amount of surrounding tissue removed depends on the characteristics and size of the growth. In the case of breast cancer, the entire breast is often removed, resulting in disfigurement of the patient and the need for reconstructive surgery. More recently, it has become acceptable to remove only the growth and a relatively small portion of surrounding tissue in a "lumpectomy" procedure to reduce trauma and the need for reconstructive surgery. However, even lumpectomies are accomplished through an open incision. Also, tissue covering the growth is dissected in order to access the growth with conventional surgical implements. Accordingly, disfigurement and the need for reconstructive surgery are not eliminated.

SUMMARY OF THE INVENTION

Accordingly, it is a primary object of the present invention to facilitate minimally invasive procedures for collecting tissue at obstructed anatomical sites.

Another object of the present invention is to create space at an obstructed anatomical site adjacent tissue to be collected allowing procedures to be carried out at the anatomical site by single puncture techniques as well as multiple puncture techniques.

A further object of the present invention is to dissect connected tissue at an obstructed anatomical site to create space at the obstructed anatomical site for collecting tissue.

An additional object of the present invention is to separate a lump from surrounding anatomical tissue to facilitate biopsy or removal of the lump.

The present invention has as an additional object to provide a method for performing minimally invasive breast biopsy.

Yet another object of the present invention is to provide a method for performing minimally invasive lumpectomy.

These and other objects, advantages and benefits are realized with the present invention as generally characterized in a method of collecting a portion of tissue at an obstructed site within anatomical tissue comprising the steps of inserting a distal end of a guide member in the anatomical tissue to position the distal end of the guide member at the obstructed site adjacent the portion of tissue to be collected, visualizing the obstructed site with an endoscope from external of the anatomical tissue, injecting a viscous, optically clear fluidic material through the guide member for release at the obstructed site to displace the anatomical tissue and create a fluid filled space in the anatomical tissue adjacent the tissue portion to be collected, introducing a distal end of a tissue collector in the space, dissecting the tissue portion to be collected from the remainder of the anatomical tissue with the distal end of the tissue collector and removing the dissected tissue portion from the anatomical tissue. Introduction of the fluidic material at the obstructed site can be used to fluidically dissect the anatomical tissue from the tissue portion to be collected. In addition, creation of the space adjacent the tissue portion to be collected exposes and presents the tissue portion to be collected in the space for visualization and access. The portion of tissue that is collected can be a specimen of a lump or other suspicious area or can be an entire lump or other suspicious area.

Some of the advantages of the present invention are that tissue collection at obstructed sites within anatomical tissue is facilitated with the creation of a space at the obstructed site for enhanced visualization and access of a tissue portion to be collected, tissue portions to be collected as well as surrounding anatomical tissue can be visually examined in situ, specimen or lump removal can be confirmed visually, tissue portions to be collected can be fluidically dissected from surrounding tissue as space is created at the obstructed site, the size of a penetration or puncture in the tissue used to access the obstructed site is minimized, trauma to anatomical tissue surrounding the tissue portion to be collected is reduced, disturbance of lumps, tumors, growths or other suspicious areas is minimized to prevent dispersal of potentially malignant cells, the surrounding anatomical tissue can fill in the space following tissue collection for minimal disfigurement, the material used to create the space can remain in the patient's body for augmentation, various tissue collectors can be used depending on whether a specimen or an entire lump is to be collected and an anchoring device can be used to engage the tissue portion to be collected prior to dissection.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 1 is a side view of an instrument for use in the methods according to the present invention.

FIG. 2 is a proximal end view of the instrument.

FIG. 3 is a sectional view of the instrument.

FIG. 4 is a side view of the instrument modified to include a housing.

FIG. 5 is a sectional view of the instrument modified to include a channel in a wall of a guide member or needle of the instrument.

FIG. 6 illustrates the instrument inserted into anatomical tissue.

FIG. 8 illustrates a tissue collector introduced in the space to collect a portion of the lump.

FIG. 9 is a side view of an alternative instrument for use in the methods according to the present invention.

FIG. 13 is a side sectional view of a distal portion of the tissue collector in a cutting position.

FIG. 14 is a broken, side sectional view of the distal portion of the tissue collector in a safety position.

FIG. 15 is a broken, top view of a proximal portion of the tissue collector.

FIG. 26 is a broken side view, partly in section, of the modified tissue collector in a fully open position.

FIG. 27 is a broken, side sectional view of the distal portion of the modified tissue collector in a fully closed position.

FIG. 28 is a sectional view of the modified tissue collector taken along line 28—28 of FIG. 24.

DETAILED DESCRIPTION OF THE PREFERRED EMBODIMENTS

Figure 7:
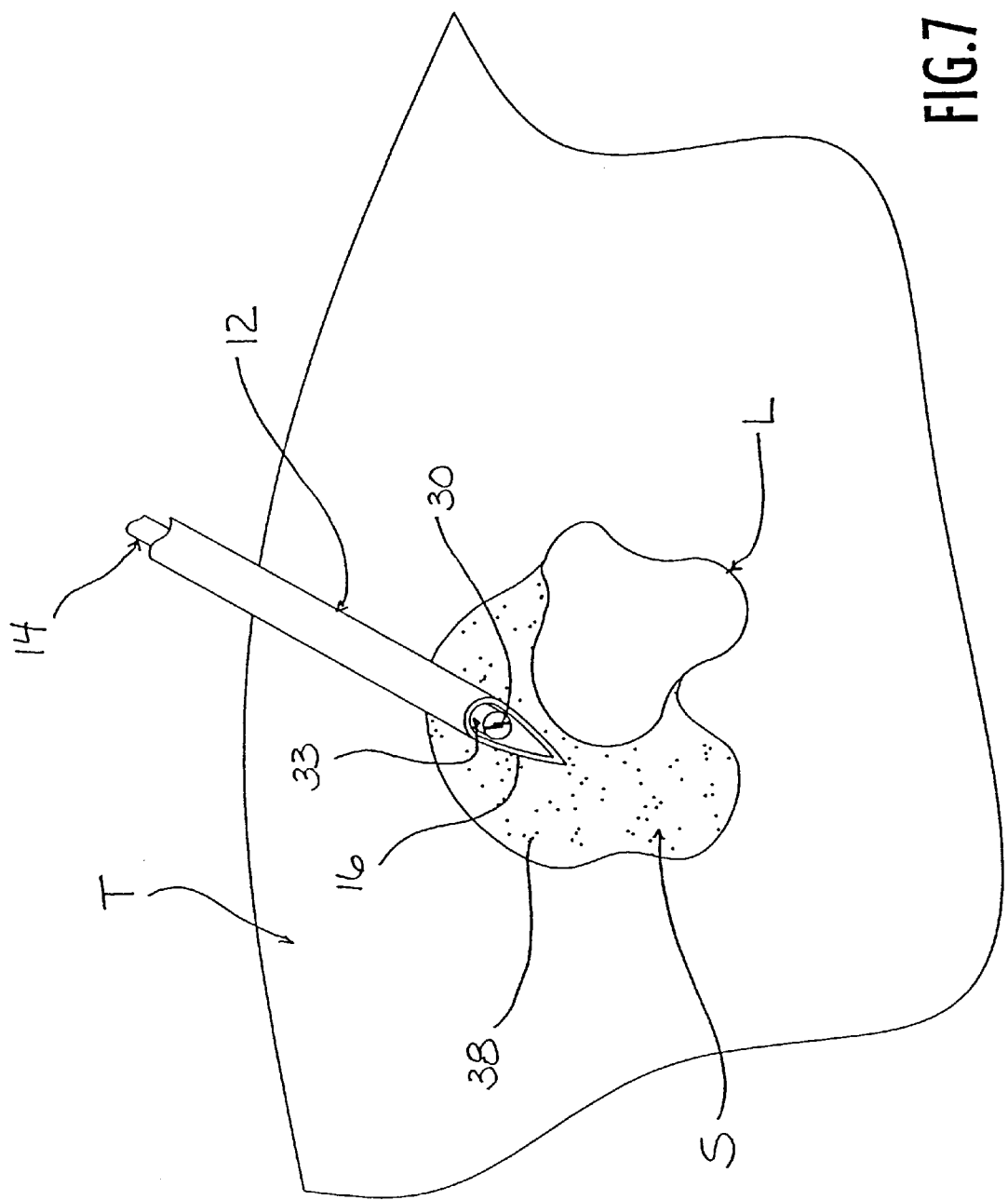
FIG. 7 illustrates a material injected through the instrument to create a space in the anatomical tissue adjacent a lump.

FIG. 1 illustrates an instrument 10 for use in a method according to the present invention. Instrument 10 includes an elongate, hollow or tubular guide member, such as a needle or cannula 12, and a micro endoscope 14 disposed in needle 12. Needle 12 has a distal end 16, a proximal end 18 and a lumen or passage therethrough receiving micro endoscope 14. The distal end 16 is configured to penetrate anatomical tissue of a patient to permit the distal end of the needle to be advanced to an obstructed site in the tissue, such as an anatomical potential or virtual space. In the case of needle 12, the distal end 16 is open and is sharp and preferably angled or beveled as shown in FIG. 1 to pierce anatomical tissue and to facilitate advancement of the needle 12 in such tissue. The proximal end 18 of needle 12 is open or includes an aperture for insertion of the micro endoscope 14 and/or another instrument into the needle lumen. Preferably, the cross sectional size of the needle lumen is only slightly larger than the cross sectional size of the micro endoscope 14, such that there is a small or narrow gap or space between the micro endoscope 14 and the needle 12 while minimizing the external cross sectional size of the needle to minimize the size of the penetration or puncture made by the needle 12 in the tissue.

Preferably, the needle 12 includes a valve or seal to prevent the egress of fluid through the proximal end 18. As an example, FIG. 2 illustrates a seal 20 at the proximal end 18 of the needle, the seal 20 including an elastic membrane 21 having a variable size hole, passage or aperture 22 therein for receiving the micro endoscope 14 or another instrument therethrough. In a natural or relaxed condition for the seal 20, the aperture 22 is closed or substantially closed. The seal 20 is stretchable or deformable to permit diametric enlargement or expansion of the aperture 22 to accommodate the external cross sectional size of the micro endoscope 14 or the external cross sectional size of another instrument inserted therethrough to be disposed within the needle lumen, the membrane 21 sealingly engaging the micro endoscope 14 or other instrument and preventing the egress of fluid through the proximal end 18 of the needle. When the micro endoscope 14 or other instrument is withdrawn from the needle 12, the seal 20 returns to its natural or relaxed condition with the aperture 22 closed or substantially closed to prevent any significant fluid egress or leakage from the proximal end 18. It should be appreciated that various single or multiple valves and/or seals can be provided in the needle to prevent the leakage or egress of fluid when the micro endoscope or another instrument is disposed in the needle lumen and when the micro endoscope or another instrument is withdrawn from the needle lumen. Such valves or seals can be designed for passage of a single instrument, such as the micro endoscope or another instrument, therethrough or for passage of multiple instruments therethrough simultaneously. Where multiple instruments, such as the micro endoscope and another instrument, therethrough or for passage of multiple instruments therethrough simultaneously. Where multiple instruments, such as the micro endoscope and another instrument, are to be passed through the valves or seals, the valves or seals can have multiple passages for receiving the multiple instruments, respectively, therethrough.

A port 24 is disposed on the needle 12 and communicates with the needle lumen. The port 24 is located on needle 12 so as to remain external of the penetrated tissue, typically external of the patient's body, and extends laterally from the needle 12. The port 24 is provided with a valve 26 for selectively opening and closing the port 24. Valve 26 is a ball cock valve having a knob 28 for manual operation thereof in a conventional manner. However, various other types of valves can be provided on the instrument 10 for selectively opening and closing the port 24.

Micro endoscope 14 has an elongate body with a distal end 30 for being disposed at the obstructed anatomical site and a proximal end coupled with a remote viewing device 32 for being disposed external of the penetrated tissue, typically external of the patient's body. The body of the micro endoscope 14 houses an illumination and imaging system (not shown in FIGS. 3 and 5) by which light is transmitted to the obstructed anatomical site from a light source external of the patient's body and by which an image of the obstructed anatomical site is transmitted to the remote viewing device 32 for visualization or observation by the surgeon. The illumination and imaging system can include various fiber optics, mirrors and lens systems, for example, for illumination and imaging. The body of endoscope 14 is of minimal or "micro" cross sectional size, being 2 mm or less in diameter. The remote viewing device 32 can be designed in many ways to provide convenient visualization. For example, the remote viewing device 32 can include an eyepiece 34 as shown in FIG. 1 and/or a video monitor. As also shown in FIG. 1, the eyepiece 34 can be adjustable as indicated in dotted lines by way of example such that the angle of the eyepiece 34 relative to a longitudinal axis of the micro endoscope 14 can be adjusted. The micro endoscope 14 can be of the types sold by Microgen and Gold. It should be appreciated that the micro endoscope 14 can be without illumination capability in which case the obstructed anatomical site can be illuminated by way of a separate illumination system, such as an illumination system carried by or housed within the needle 12 as discussed further below or a separate illumination instrument.

The instrument 10 is assembled as shown in FIG. 1 with the micro endoscope 14 extending through the aperture 22 of seal 20 such that the body of the endoscope extends through the membrane 21 and is sealingly gripped thereby. The micro endoscope 14 is concentrically disposed in the needle 12; and, since the external cross sectional size of the micro endoscope 14 does not completely fill the needle lumen, there is a circumferential or radial gap or space between endoscope 14 and needle 12 as shown in FIG. 3. The gap or space defines a channel 33 proximally coupled with port 24 and distally communicating with an obstructed anatomical site at which the distal end 16 of the needle 12 is introduced, the channel 33 being formed by an unoccupied portion of the needle lumen when the endoscope 14 is disposed therein. Although channel 33 is formed by a concentric, circumferential gap or space due to the concentric arrangement of needle 12 and endoscope 14, it should be appreciated that the endoscope 14 can be disposed in the needle lumen non-concentrically, such as eccentrically, in which case the gap or space forming channel 33 will be non-concentric with the needle. Of course, the location of aperture 22 can vary in accordance with a desired arrangement for micro endoscope 14 in the needle lumen.

The distal end 30 of the micro endoscope 14 is typically aligned with the distal end 16 of the needle 12 prior to penetration of the anatomical tissue by the needle 12, and the remote viewing device 32 is disposed proximally of the proximal end 18 of the needle. It should be appreciated that the longitudinal position of the distal end 30 of micro endoscope 14 relative to the needle 12 can be adjusted during use and that the distal end 30 of the micro endoscope can be moved or advanced distally beyond the distal end 16 of the needle 12 as shown in dotted lines in FIG. 1 and can be moved proximally into the needle 12. The longitudinal position of the micro endoscope 14 relative to the needle 12 is maintained due to the sealing grip of the seal 20 on the body of the endoscope, and the micro endoscope 14 can be manually moved longitudinally, proximally and distally, relative to the needle 12 by overcoming the frictional gripping or sealing force of the seal 20 to position the distal end 30 for optimal viewing. It should also be appreciated that the instrument 10 can be provided with various releasable detents or locking mechanisms to selectively, releasably fix the longitudinal position of the micro endoscope 14 relative to the needle 12.

FIG. 4 illustrates instrument 10 as modified to include a housing 36 mounting the proximal end of the needle 12 and having a passage therethrough through which the micro endoscope 14 or another instrument can be introduced into the lumen of needle 12. The housing 36 can include various single or multiple valves and/or seals therein for preventing the egress of fluid therefrom when the micro endoscope and/or another instrument passes therethrough and when the micro endoscope 14 and/or another instrument is withdrawn from housing 36.

FIG. 5 illustrates needle 12 modified to include a channel 33' formed in the thickness of the wall forming needle 12. Channel 33' communicates proximally with the port 24 and communicates distally with an obstructed site at which the distal end of the needle is introduced. Channel 33' is separate from and does not communicate with the needle lumen such that the cross sectional size of the needle lumen can be no larger than necessary to accommodate the external cross sectional size of the endoscope 14 as shown in FIG. 5 wherein the endoscope 14 occupies the entire cross sectional size of the needle lumen. It should be appreciated that the needle 12 can be designed with both channels 33 and 33' and that, where two channels are provided, the channels can be coupled with the same port 24 or with separate ports, respectively.

FIGS. 6–8 illustrate one method of collecting tissue at an obstructed anatomical site, the procedure shown in FIGS. 6–8 being representative of a procedure wherein a tissue specimen is collected from a lump, growth, tumor or other suspicious area. As shown in FIG. 6, the distal end 16 of needle 12 is used to penetrate anatomical tissue T. The needle 12, with the micro endoscope 14 disposed therein, is advanced distally in the tissue T to an obstructed site to position the distal end 16 of the needle 12 adjacent a lump, growth, tumor or suspicious area L to be biopsied as shown in FIG. 6. The site or location in tissue T at which the distal end 16 of needle 12 is introduced is "obstructed" in that the lump L to be biopsied is surrounded by tissue T with no actual space in tissue T by which the lump L can be visualized and/or accessed with instruments. Positioning of the distal end 16 of the needle 12 at the obstructed anatomical site is visualized external of the tissue T, typically external of the patient's body, via the remote viewing device 32, which is not shown in FIGS. 6–8. In the illustrated procedure, the distal end 16 of needle 12 is positioned between or substantially between the lump L and tissue T as shown in FIG. 6, the position of the distal end 16 being confirmed with the remote viewing device through visualization of lump L adjacent the distal end 16.

Once proper positioning of the needle 12 has been confirmed visually with the micro endoscope 14, a viscous, optically clear, medically acceptable fluidic material 38 is injected through the port 24 and the channel 33, and/or the channel 33' if the needle 12 is so designed, to exit the distal end 16 of needle 12 and be released at the obstructed site. The injection of fluidic material 38 displaces and/or compresses tissue T and creates an actual, fluid filled space S at the obstructed site adjacent the lump L. In addition, by positioning the distal end 16 of needle 12 between the lump L and the surrounding tissue T, injection of the fluidic material 38 causes separation of the tissue T from the lump L as shown in FIG. 7. Where the lump L is connected to the tissue T, injection of the fluidic material 38 causes dissection of the tissue T from the lump L as the space S is created. Accordingly, the lump L is presented or exposed in the space S and is accessible via the needle 12 and space S. Creation of space S and exposure of lump L is visualized external of the tissue T via the remote viewing device 32, and the lump L can be visually examined. Even though the space S contains fluidic material 38, the needle 12 and the micro endoscope 14, as well as other instruments introduced in space S, can be easily manipulated in the space S and can access or contact the lump L due to the fluidic nature of the material 38, and the endoscope 14 can be used for remote viewing due to the optical clarity or transparency of material 38. The valve 26 for port 24 and the seal 20 prevent the egress or leakage of fluidic material 38 and thusly retain the material 38 in space S.

With the visualization and access room provided by space S and with exposure of lump L in space S, a specimen or portion of lump L is obtained for biopsy. FIG. 8 illustrates a distal end of a tissue collector 40, such as a specimen collector or biopsy instrument, introduced in space S through a second penetration or puncture in tissue T. Accordingly, the procedure illustrated in FIGS. 6–8 is representative of a multiple puncture or multiple penetration procedure and, more specifically, a two puncture procedure. The distal end of the tissue collector 40 is used to dissect and collect a portion or specimen of lump L under visualization provided by the micro endoscope 14. The distal end of tissue collector 40 includes pivotable biopsy jaws 41 for cutting a tissue specimen and capturing or retaining the cut specimen within the jaws in a conventional manner. Following dissection and capture of the specimen, the tissue collector 40 is withdrawn from the tissue T, and the specimen is retrieved external of the patient's body for identification and analysis. Once the tissue collector 40 has been withdrawn and the specimen has been retrieved external of the patient's body, the instrument 10 is withdrawn from the patient's body, and the penetration or puncture sites in tissue T are attended to in a conventional manner.

Various types of conventional biopsy instruments having various distal end structure for dissecting and, preferably, capturing, holding or retaining, a portion or specimen of tissue can be used as the tissue collector. Suction can be utilized in the tissue collector 40 for withdrawing the specimen from the patient's body. Depending on the type of fluidic material 38 utilized to create space S, the fluidic material can remain in the patient's body temporarily to be naturally dissipated or absorbed or, alternatively, permanently for augmentation. In the former case, the fluidic material should be capable of safely being absorbed or dissipated by the patient naturally; and, in the latter case, the fluidic material should be capable of remaining in the patient's body for an extended period of time without significant adverse consequences. However, it should be appreciated that prior to withdrawal of the instrument 10 from the patient's body, the fluidic material 38 can be released from the space S through port 24 by opening valve 26 and/or can be aspirated or withdrawn from the patient's body. For example, the port 24 can be connected or coupled with a source of vacuum or suction for aspiration of fluidic material 38 or other substances through the channel 33 and/or the channel 33'. It should be appreciated that the size of space S can be adjusted during use. More particularly, the space S can be made larger by injecting additional fluidic material through needle 12 and can be made smaller by releasing or withdrawing fluidic material from space S through port 24. Where the needle has multiple channels coupled with separate ports, respectively, it should be appreciated that one port and associated channel can be used to inject the fluidic material and/or other substances at the obstructed site, and another port and associated channel can be used to withdraw the fluidic material and/or other substances from the patient's body. Where the fluidic material 38 dissipates or is absorbed naturally or is aspirated or otherwise released from the patient's body, the tissue T will, where sufficiently resilient, naturally decompress or move to fill in the space S such that there is minimal disfigurement for the patient. Where suction is used to aspirate the fluidic material 38 from the tissue, such suction can be used to draw the tissue T to fill in the space S. Where a relatively large tissue portion is collected and/or where the tissue is not sufficiently resilient, all or some of the fluidic material can be left in the patient's body to fill in the space S and/or the space or void left by the removed tissue portion for permanent augmentation. In the latter case, a fluidic material that is not naturally absorbable or capable of being broken down by biological processes can be used provided the fluidic material can safely remain in the patient's body. Although FIGS. 6–8 illustrate a multiple puncture procedure for collecting a tissue portion, it should be appreciated that all of the instruments utilized during the procedure can be introduced in the tissue T through a single penetration or puncture. As an example, both the micro endoscope 14 and the tissue collector 40 can be received in the lumen of needle 12 as discussed further below.

Various optically clear or transparent, viscous, medical grade fluidic materials can be used in the methods of the present invention. A preferred fluidic material being high density glucose or compositions thereof, such as Hyskon made by Medisan Pharmaceuticals Inc. The same fluidic material or a combination of different fluidic materials can be introduced at the obstructed site in a given procedure for space creation and/or fluidic dissection of tissue as well as other functions such as cleansing and supplying medicaments such as anesthetics. The fluidic material or materials is/are injected at the obstructed site under sufficient pressure to displace the tissue to create a space at the obstructed site, and such pressure can be selected or adjusted in accordance with the nature of the tissue and the force required to displace the tissue. Where surrounding tissue is connected or attached to a lump, the injection pressure can be selected or adjusted in accordance with the force required to dissect the surrounding tissue from the lump. By controlling the injection pressure, fluidic dissection and/or space creation can be accomplished with minimal trauma or damage to surrounding tissue and minimal disturbance of the lumps as not to disperse potentially malignant cells.

FIG. 9 illustrates at 110 another embodiment of an instrument for use in the methods of the present invention, the instrument 110 being representative of an instrument wherein the micro endoscope and the tissue collector are both disposed within the lumen of the guide member. Instrument 110 includes needle 112, micro endoscope 114 for being received in needle 112, an anchoring device 142 that can be inserted through needle 112 and a tissue collector 140 (a proximal end of which is illustrated in phantom in FIG. 9) that can be inserted through anchoring device 142. Needle 112 and micro endoscope 114 are similar to needle 12 and micro endoscope 14, respectively, the endoscope 114 having a remote viewing device 132 made as an eyepiece 134 offset from or disposed at an angle with the body of the endoscope 114. Anchoring device 142 is the same as the anchoring device disclosed in application Ser. No. 60/050, 092 incorporated herein by reference and includes a tubular body defining an operating channel therethrough through which tissue collector 140, or another instrument, can be inserted and/or through which the fluidic material and/or other substances can be introduced and/or withdrawn from the patient's body. The anchoring device 142 has a proximal end 144 that is open or is provided with an aperture to access the operating channel, and a valve 146 of the anchoring device 142 selectively opens and closes the operating channel to selectively permit tissue collector 140, or another instrument, to be inserted therethrough and/or to selectively permit the fluidic material and/or other substances to be supplied to and/or withdrawn from the patient's body when the tissue collector or other instrument is not disposed in the operating channel or does not occupy the operating channel completely.

Figure 11:
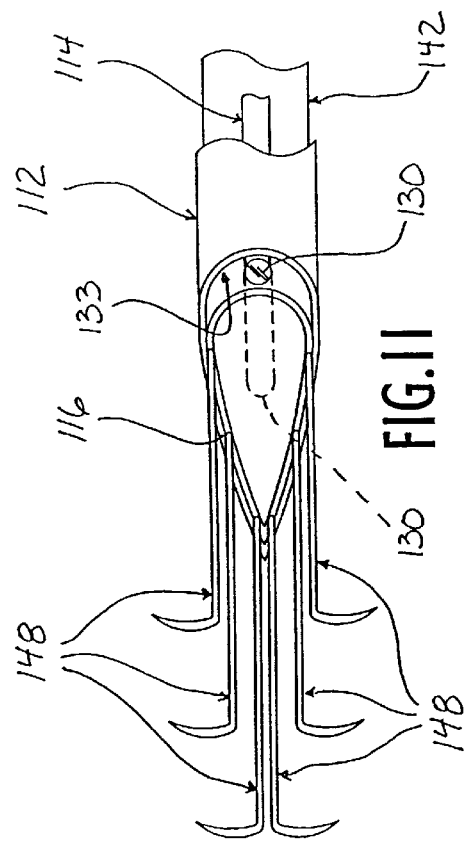
FIG. 11 is a top view of a distal portion of the alternative instrument illustrating tongs of the anchoring device extended from the guide member or needle of the alternative instrument.
Figure 10:
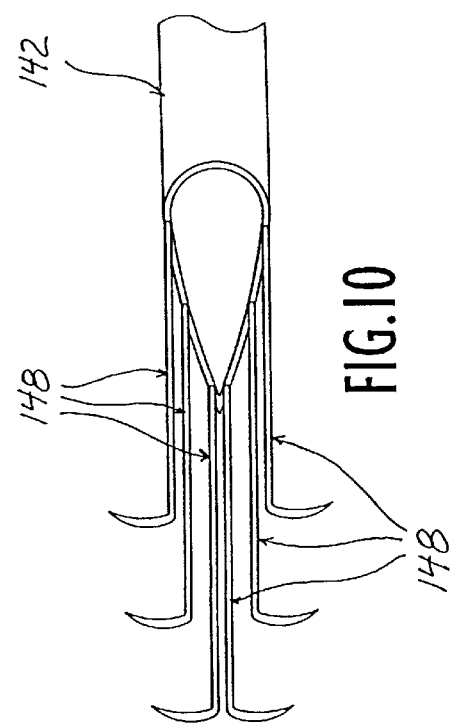
FIG. 10 is a top view of a distal portion of an anchoring device of the alternative instrument.

As best illustrated in FIG. 10, which shows a distal portion of anchoring device 142, anchoring device 142 includes flexible tongs 148 formed on a distal end of the tubular body of anchoring device 142. Tongs 148 can be formed integrally, unitarily with the tubular body of anchoring device 142 or can be fixedly or removably attached to the tubular body. In the case of anchoring device 142, a distal end of the tubular body is angled or beveled to correspond to the angle of the distal end 116 of needle 112. However, the distal end of the tubular body can have any appropriate configuration depending on the particular application. Tongs 148 are made of a flexible, resilient material or a material having shape memory, such as spring material, and extend from an edge of the distal end of the tubular body of anchoring device 142. Tongs 148 each are constituted of a generally straight portion extending distally from the edge of the distal end of the tubular body and an arcuate outwardly extending portion extending angularly or laterally outwardly from the straight portion in a natural or relaxed position for tongs 148 as shown in FIG. 10. When the tongs 148 are disposed in needle 112, the tongs 148 are in a compressed position with the outwardly extending portions of the tongs compressed or deflected as shown in phantom in FIG. 9 such that the arcuate portions are longitudinally aligned with the straight portions, respectively. FIG. 11 illustrates tongs 148 returned to the natural or relaxed position after being extended distally from the distal end 116 of needle 112 when the anchoring device 142 is advanced longitudinally, distally through the needle 112 as described further below. The number of tongs and the configuration and arrangement thereof can vary in accordance with procedural use and practical considerations as disclosed in the prior application Ser. No. 60/050,092 incorporated herein by reference.

Figure 12:
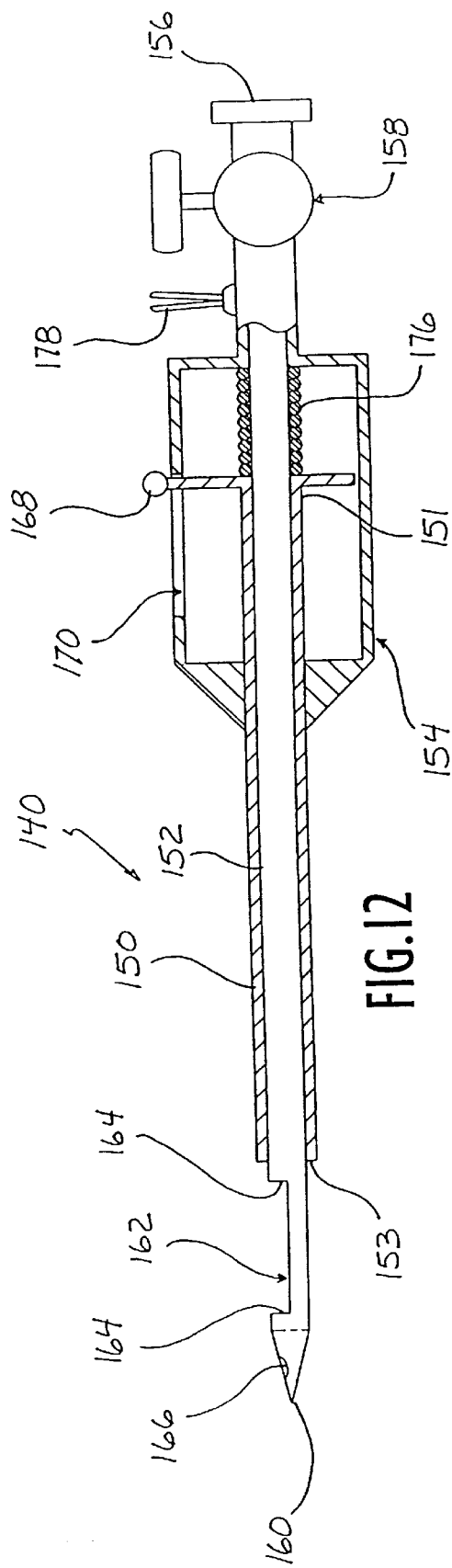
FIG. 12 is a side sectional view of a tissue collector of the alternative instrument.

Tissue collector 140 shown in FIG. 12 is the same as the specimen collector disclosed in the prior application Ser. No. 60/050,092 incorporated herein by reference and includes an outer tubular member 150, an inner tubular member 152 disposed in outer tubular member 150 and a housing 154 mounting proximal ends of the outer and inner tubular members 150 and 152, respectively. Inner member 152 terminates proximally at a proximal end 156 that is open or is provided with an aperture providing access to the lumen of the inner tubular member 152, and the inner tubular member 152 has a valve 158 for selectively opening and closing the inner tubular member lumen. The inner tubular member 152 terminates distally at a sharp, conical tip 160 that is adapted to be driven into a lump or other tissue to be biopsied. A slot 162 is formed in a distal end of the inner tubular member 152 to define an open space between longitudinally spaced edges 164 that extend along a portion of the circumference or cross sectional periphery of inner member 152. A hole 166 is formed in tip 160 to permit instruments inserted in the lumen of the inner member 152 to access an anatomical site at which tip 160 is introduced or to be used for injection of the fluidic material and/or other substances and/or for aspiration of the fluidic material and/or other substances and/or for visualization, for example.

Outer tubular member 150 has a proximal end 151 slidably disposed in housing 154 and a distal end 153 that extends beyond tip 160 when the outer member 150 is advanced distally relative to the inner member 152 as shown in FIG. 14. A sharp cutting edge 167 is defined on the distal end 153 of outer member 150. A knob 168 extends from the proximal end 151 of outer member 150 and through a slot 170 formed in a wall of housing 154. As shown in FIG. 15, slot 170 has a first transverse portion 172, a second transverse portion 174 and a longitudinal portion 175 between the first and second transverse portions, it being noted that knob 168, which has a stem that slides along slot 170, is not illustrated in FIG. 15 for the sake of clarity. A biasing member 176, shown as a coiled spring, biases outer member 150 distally to a safety position shown in FIG. 14. In the safety position, the stem of knob 168 is received in first transverse portion 172 of slot 170 and the distal end 153 of outer member 150 extends beyond and covers the tip 160 of inner member 152 to protect surrounding structure from being damaged by tip 160 as tissue collector 140 is inserted through anchoring device 142 in the manner described below. Outer member 150 can be retracted by sliding the stem of knob 168 along longitudinal portion 175 of slot 170 to rest in second transverse portion 174 thereby exposing slot 162 and edges 164 as shown in FIG. 12. Reversing this motion will cause the outer member 150 to slide over slot 162 as shown in FIG. 13 to cut or dissect anatomical tissue disposed in the slot 162 as described further below. The inner member 152 can have various distal end configurations including those disclosed in the prior application Ser. No. 60/050,092 incorporated herein by reference. As shown in FIG. 12, the tissue collector 140 can include a connector 178 to permit an energy source, such as an electrical power source, to be coupled to inner member 152 allowing the tissue collector to be used for unipolar or bipolar cauterization or other energy application such as laser, ultrasound and cryoenergy.

Figure 16:
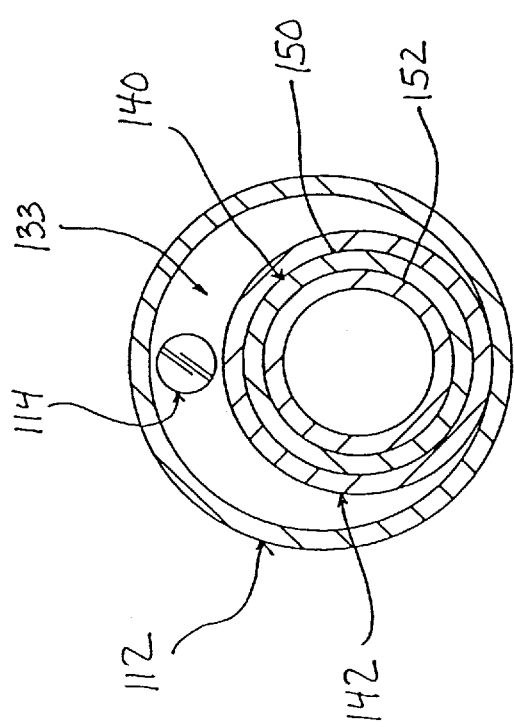
FIG. 16 is a sectional view of the alternative instrument.

FIGS. 9 and 16 illustrate one manner of arranging the micro endoscope 114, the anchoring device 142 and the tissue collector 140 in the lumen of needle 112. As best shown in FIG. 16, the tissue collector 140 is disposed within the anchoring device 142, and the micro endoscope 114 and the anchoring device 142 are eccentrically arranged within the lumen of needle 112. The micro endoscope 114 and the anchoring device 142 together do not completely fill the cross section of the needle lumen leaving a gap or space within needle 112 forming channel 133 through which the fluidic material and/or other substances can be injected and/or withdrawn via port 124 as described above for instrument 110. It should be appreciated, however, that the fluidic material does not have to be injected and/or withdrawn through the channel 133 within the needle 112 since the lumen of the inner tubular member 152 of the tissue collector 140 can be used to inject and/or withdraw the fluidic material. In addition, the operating channel of the tubular body of anchoring device 142 can be larger in cross section than the external cross section of the tissue collector 140 so that the operating channel is not completely filled by the tissue collector 140. In the latter case, there will be a gap or space within the tubular body of the anchoring device 142 between the tissue collector 140 and the anchoring device tubular body, and such gap or space can be used to inject and/or withdraw the fluidic materials. The operating channel of the anchoring device 142 can also be used for injection and/or withdrawal of the fluidic material by merely withdrawing the tissue collector 140 therefrom.

Figure 17:
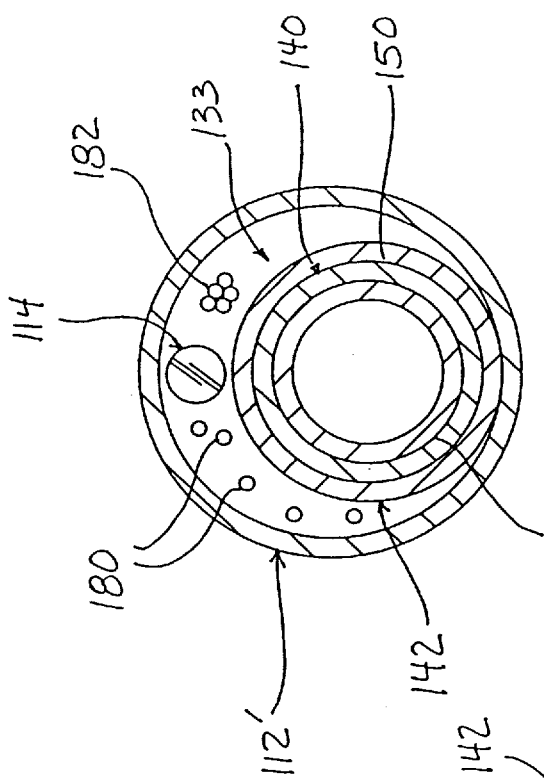
FIG. 17 is a sectional view of the alternative instrument modified to include an illumination system in the needle.

FIG. 17 illustrates instrument 110 as modified to include needle 112' designed to provide illumination at an obstructed site. Needle 112' is similar to needle 112 except that needle 112' includes an illumination system comprising optical fibers 180, or alternatively, bundles 182 of optical fibers, in the channel 133 of the needle 112'. The optical fibers provide illumination at the distal end of the instrument 110 such that the endoscope 114 need only be provided with an imaging system to perform an imaging function.

Figure 18:
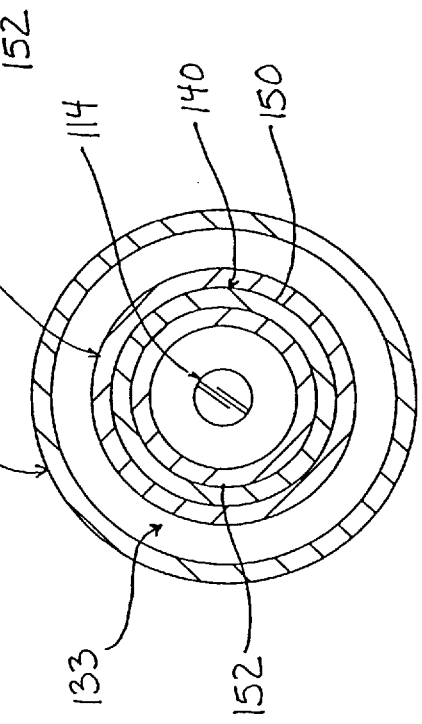
FIG. 18 is a sectional view of the alternative instrument modified to receive a micro endoscope of the alternative instrument within the tissue collector.

FIG. 18 illustrates an alternative arrangement for the endoscope 114, anchoring device 142 and the specimen collector 140 within the needle 112. FIG. 18 illustrates the anchoring device 142 concentrically disposed in the lumen of needle 112 with a circumferential gap or space therebetween defining channel 133 coupled with port 124. The tissue collector 140 is concentrically arranged within the anchoring device 142, and the endoscope 114 is concentrically disposed in the lumen of the inner tubular member 152 of the tissue collector 140. In this case, visualization by the endoscope 114 is possible through hole 166. Various other alternative arrangements for the needle, the endoscope, the anchoring device and the tissue collector are disclosed in the prior application Ser. No. 60/050,092 incorporated herein by reference.

Figure 19:
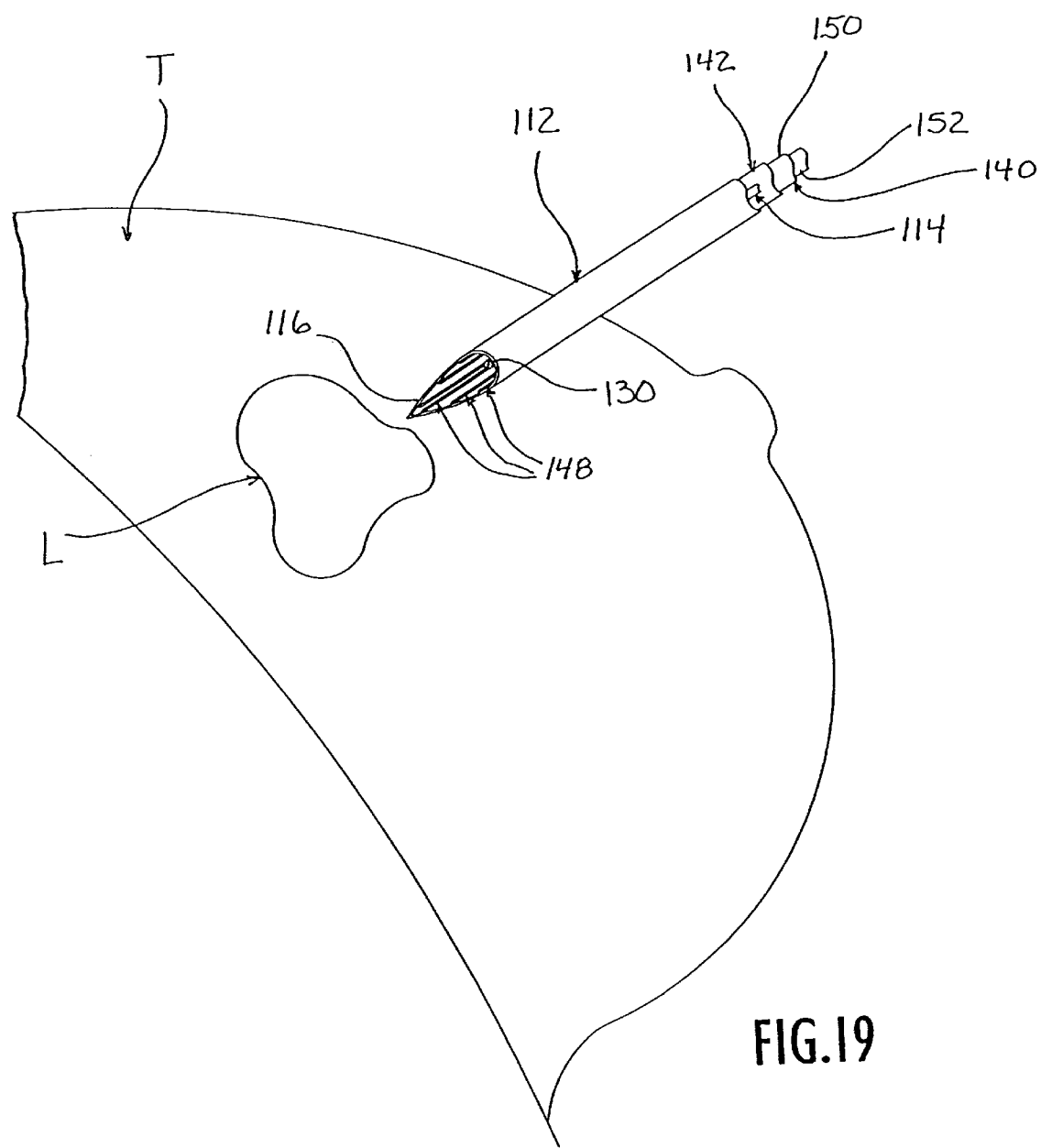
FIG. 19 illustrates the alternative instrument inserted in breast tissue.
Figure 20:
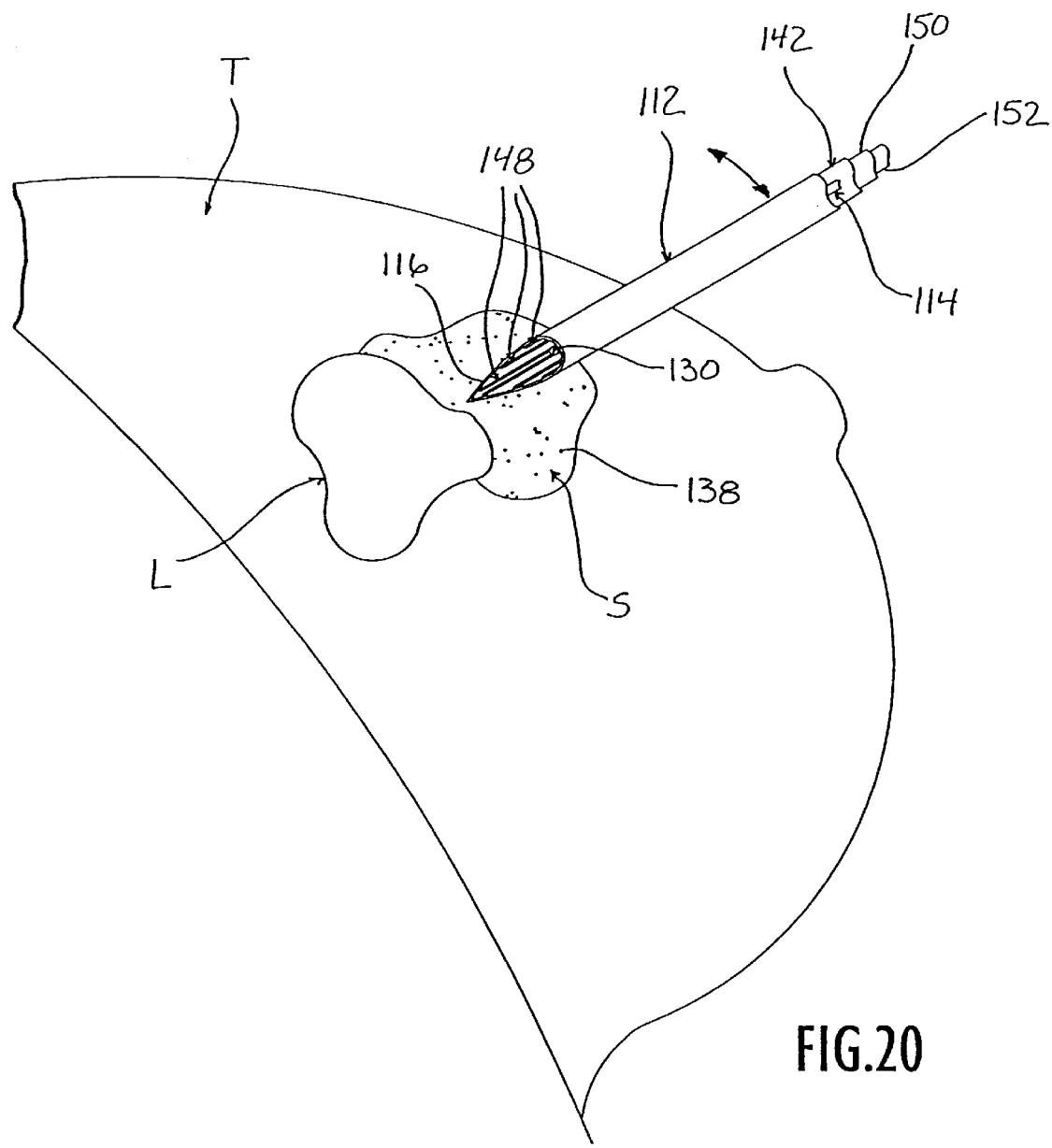
FIG. 20 illustrates material injected in the breast tissue through the alternative instrument to create a space in the breast tissue adjacent a lump.

FIGS. 19–22 illustrate collection of a tissue specimen using the instrument 110 and, in particular, illustrate a procedure for collecting a tissue specimen from a lump in breast tissue. However, the procedure described and illustrated herein can be applied to biopsy any anatomical tissue and is particularly suited for procedures on abnormal growths or areas surrounded by soft tissue. As illustrated in FIG. 19, needle 112 is inserted into breast tissue T by puncturing the skin with distal end 116 and pushing needle 112 distally or forwardly from its proximal end. The endoscope 114 is used to track the position of distal end 116 by providing visualization of the insertion procedure external of the patient's body via the eyepiece 134. Accordingly, conventional imaging techniques, such as mammography, are not needed to ascertain the position of the needle 112 thusly protecting the patient from exposure to electromagnetic radiation or other harmful energy. Of course, conventional imaging techniques, such as mammography, can still be utilized to confirm the position of the distal end 116 of the needle 112. As illustrated in FIG. 20, the distal end 116 of needle 112 is guided by the surgeon to a position adjacent the lump L as confirmed through visual observation of lump L with endoscope 114. The site at which the distal end 116 of needle 112 is positioned is obstructed since the lump L is surrounded by soft breast tissue T with no space in tissue T by which lump L can be accessed. During the insertion process, anchoring device 142 and/or tissue collector 140 can be disposed within the lumen of the needle 112 with tongs 148 contained in needle 112, as illustrated, or only the micro endoscope 114 can be disposed within the needle 112 with the anchoring device 142 and the tissue collector 140 inserted into the needle 112 following confirmation of proper positioning of the needle distal end 116.

After the distal end 116 of needle 112 has been properly positioned in relation to lump L, fluidic material 138, which can be the same as fluidic material 38, is introduced through port 124 and channel 133 for release at the obstructed site. The fluidic material 138 is released from the distal end 116 of the needle 112 into the tissue T causing compression and/or displacement of the tissue T such that an actual space S is created at the obstructed site as shown in FIG. 20. In addition, as the fluidic material 138 is directed between the lump L and the tissue T, the tissue T is fluidically dissected or separated from lump L as the space S is created. In order to facilitate dissection or separation of tissue T from lump L, the needle 112 can be angularly or pivotably moved relative to lump L as shown by the arrow in FIG. 20 to optimally position the distal end 116 for tissue dissection with minimal trauma or disturbance to tissue T and lump L. Creation of space S and the accompanying dissection or separation of lump L from tissue T presents and exposes the lump L in the space S for ready access by the anchoring device 142 and tissue collector 140, or another instrument disposed in the needle 112, and the lump L can be visually examined external of the patient's body with the micro endoscope 114. The seal at the proximal end of needle 112 and the valves 126, 146 and 158 prevent the egress of fluidic material 138 and retain the fluidic material 138 in the patient's body.

Figure 21:
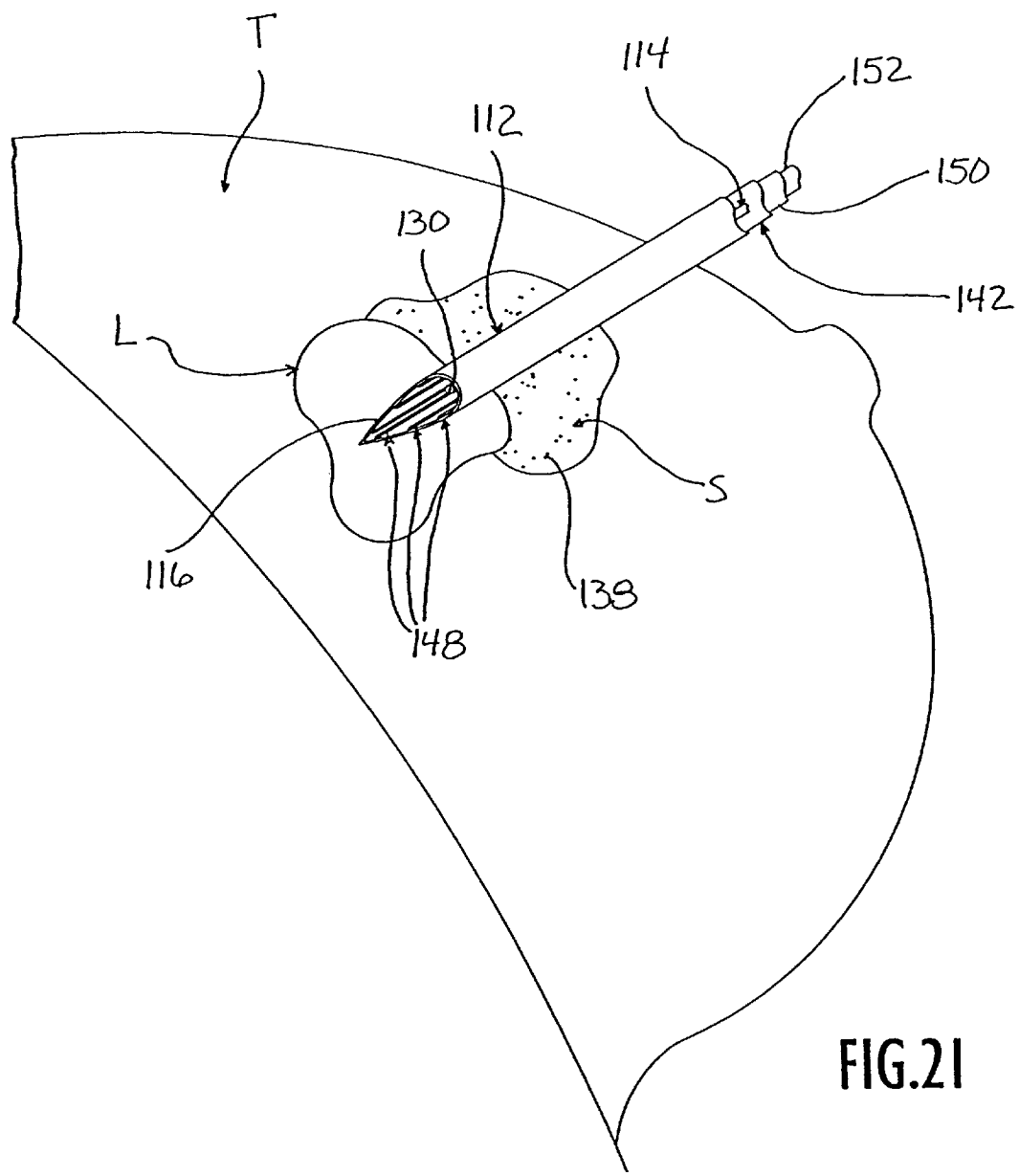
FIG. 21 illustrates the needle of the alternative instrument penetrating the lump.
Figure 22:
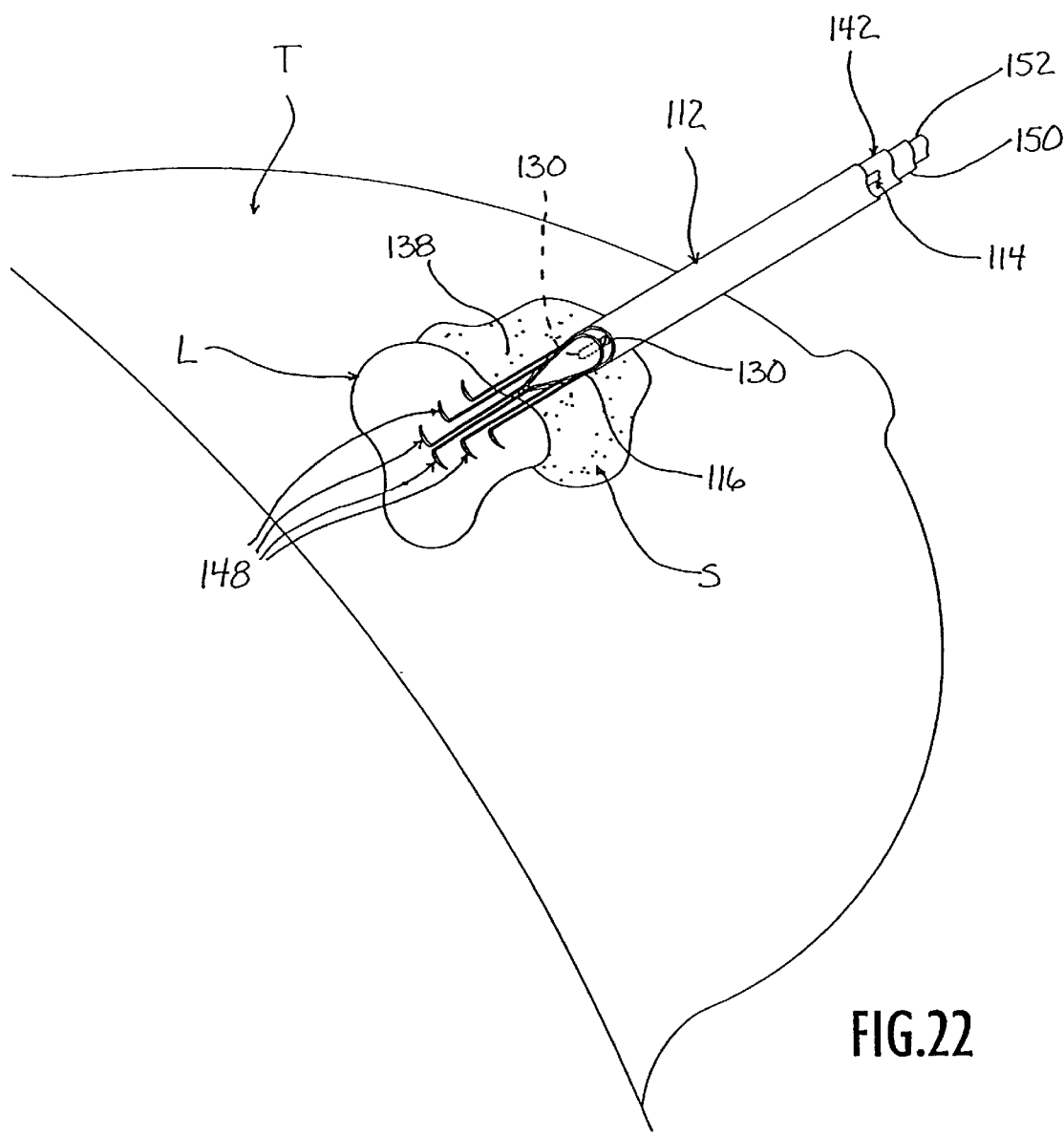
FIG. 22 illustrates the needle of the alternative instrument moved proximallyfrom the lump to expose tongs of the anchoring device.

Following creation of space S, the distal end 116 of needle 112 is driven into the lump L as shown in FIG. 21, the anchoring device 142 being moved with the needle 112 such that the tongs 148 are disposed in the lump L. Entry of the distal end 116 of the needle 112 into lump L can be confirmed visually by observing the characteristics of lump L with the eyepiece 134. As shown in FIG. 22, the needle 112 is retracted or moved proximally relative to anchoring device 142 for withdrawal from lump L while the anchoring device 142 is maintained in position and is not moved. In response to retraction of needle 112, the tongs 148 flex outward and return to their natural or relaxed position so that the tongs 148 extend into lump L as shown in FIG. 22. Accordingly, the anchoring device 142 will be firmly attached to lump L by tongs 148. Collection of a specimen of lump L can now be accomplished through the operating channel of anchoring device 142 while grasping lump L without the need for a second penetration or puncture. The endoscope 114 can be moved proximally and/or distally relative to needle 112 and/or anchoring device 142 as shown in dotted lines in FIG. 22 for optimal visualization.

Figure 23:
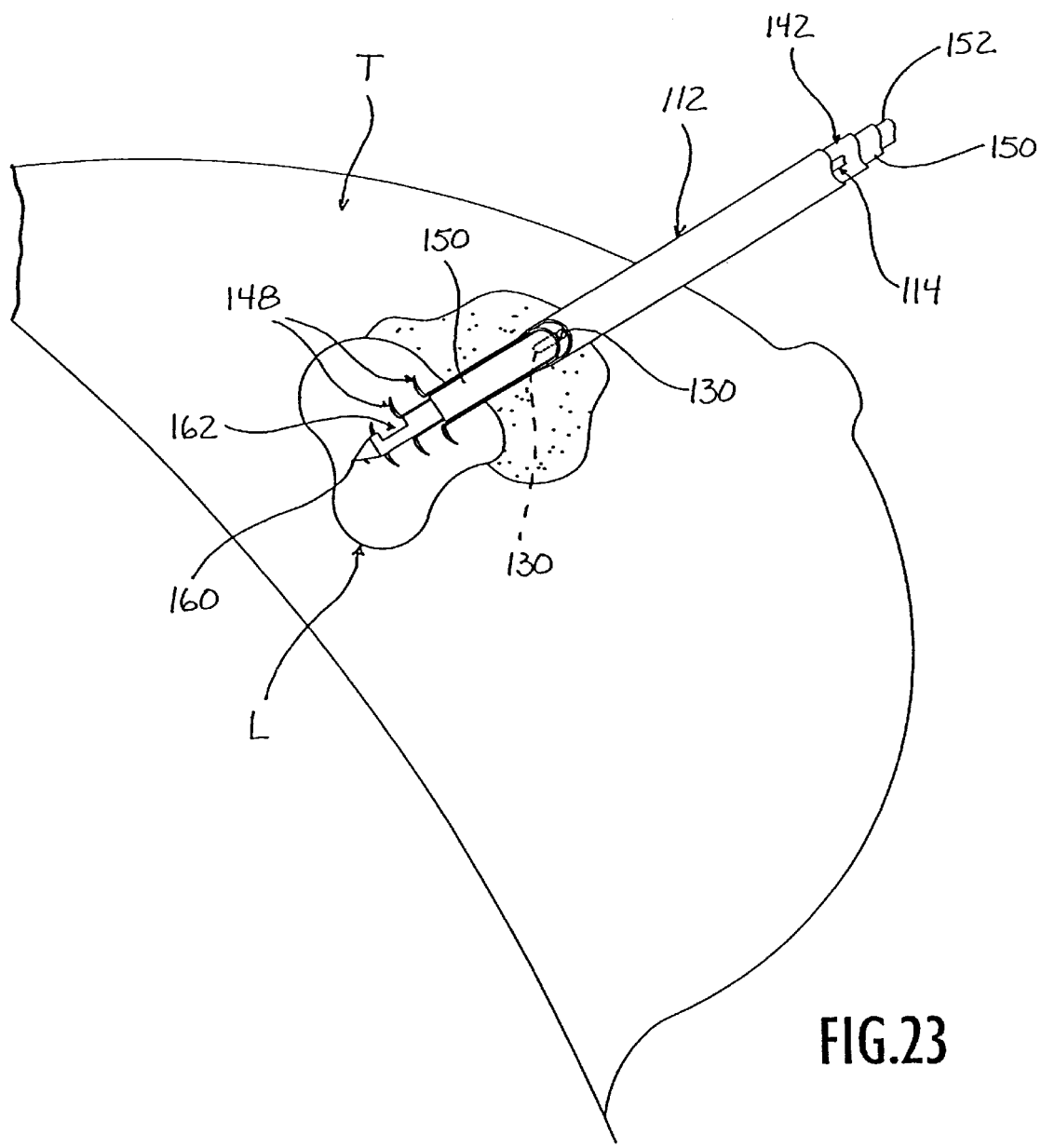
FIG. 23 illustrates a distal end of the tissue collector advanced into the lump to collect a specimen of the lump.

To collect a specimen of lump L, valve 146 is opened and tissue collector 140 is inserted through the operating channel of anchoring device 142 if the tissue collector 140 has not already been positioned inside the anchoring device 142. The tissue collector 140 is moved distally within the anchoring device 142; and, once the distal end of outer member 150 has entered the space S, the outer member 150 is retracted relative to the inner member 152 for movement from the safety position to expose the tip 160 of inner member 152. The tissue collector 140 is advanced further distally such that the tip 160 of inner member 152 pierces lump L to position slot 162 therein as shown in FIG. 23. Penetration of lump L by tip 160 and entry of slot 162 into lump L is visually confirmed with the micro endoscope 114, which can be advanced distally relative to the needle 112, the anchoring device 142 and the tissue collector 140 as shown in dotted lines in FIG. 23 to optimize viewing. Also, characteristics of lump L can be viewed with endoscope 114 for visual diagnosis and confirmation as lump L is held in place by anchoring device 142. Entry of tip 160 into lump L causes tissue from lump L to be pushed into slot 162. Once this has occurred, knob 168 is moved distally to move outer member 150 across slot 162 to the position shown in FIG. 13. This causes a portion of lump L to be cut by cooperation of the distal cutting edge 167 of outer member 150 with edges 164 formed on inner member 152. The cut portion of lump L will be retained in slot 162, and suction can be applied to inner member 152 to pull the cut portion of lump L, i.e., the specimen, proximally to permit another specimen to be cut and retained. A plurality of specimens can be cut and retained in inner member 152 in this manner, if desired. Also, specimens can be suctioned from the proximal end of inner member 152 for analysis without removing the tissue collector 140 from the patient's body. When tissue collection is finished, the instrument 110 is withdrawn from the tissue T. If necessary, needle 112 can be moved distally over tongs 148 to compress and contain tongs 148 to facilitate removal of the instrument 110.

Various tissue collectors can be used in the methods of the present invention including the various specimen collectors disclosed in the prior application Ser. No. 60/050,092 incorporated herein by reference. Where the micro endoscope 114 is disposed within the tissue collector 140 during tissue collection, visualization of the procedure is possible via the hole 166. The needle and the anchoring device can be mounted on a housing to form an integral device, and handle structure can be provided for moving the needle and/or the anchoring device relative to the other of the needle and/or the anchoring device as disclosed in the prior application Ser. No. 60/050,092 incorporated herein by reference.

If analysis of a biopsy specimen or visual imaging indicates that a particular lump is malignant or otherwise dangerous because of its size or other characteristics, it is desirable to remove the lump. When a lump in breast tissue is to be removed, a procedure known as a "lumpectomy", in which only the lump and a small portion of surrounding tissue are removed is often undertaken.

Figure 25:
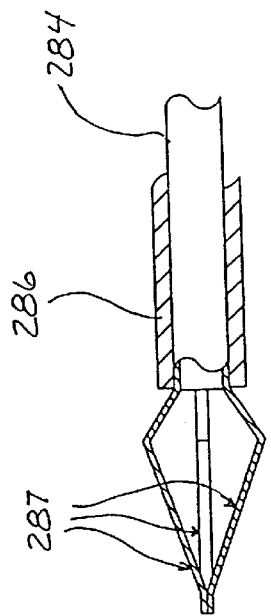
FIG. 25 is a broken, side sectional view of the distal portion of the modified tissue collector in a partially closed position.
Figure 24:
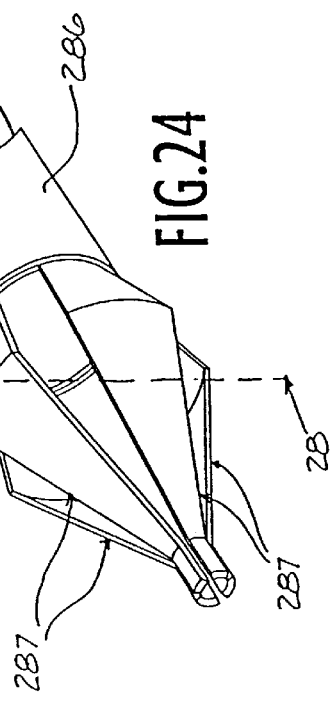
FIG. 24 is a broken perspective view of a distal portion of a modified tissue collector for use in the methods according to the present invention to collect an entire lump.

FIGS. 24–28 illustrate an alternative tissue collector 240 in the nature of a dissecting instrument for removing or collecting an entire lump from tissue, particularly soft tissue such as breast tissue, in accordance with the methods of the present invention. Tissue collector 240 is substantially the same as the dissecting instrument disclosed in Ser. No. 60/050,092 incorporated herein by reference and can be inserted into tissue, particularly soft tissue such as breast tissue, through anchoring device 142 or through a second penetration or puncture to separate a lump from surrounding tissue and remove the lump. Tissue collector 240, a distal portion of which is illustrated in FIGS. 24, 25 and 27, includes tubular inner member 284 and tubular outer member 286 that is axially slidable relative to inner member 284. Inner member 284 has a plurality of arms 287 extending from a distal end thereof, four arms 287 being provided in the illustrated embodiment. Arms 287 are made of a resilient or flexible material or a material having shape memory, such as spring material, and naturally assume a fully open position in which the arms 287 extend outwardly from inner member 284 as shown in FIG. 26. However, when the outer member 286 is sufficiently advanced distally beyond the distal end of inner member 284, as shown in FIG. 27, arms 287 are pressed toward one another to a fully closed position, wherein arms 287 are confined substantially within the radial dimensions of outer member 286. In the fully closed position, tissue collector 240 can be inserted through anchoring device 142, a portal sleeve, or other aperture or passage, into soft tissue. Adjustment of the longitudinal or axial position of outer member 286 relative to inner member 284 can cause arms 287 to assume any position between the fully open position of FIG. 26 and the fully closed position of FIG. 27, such as the partially open position illustrated in FIGS. 24 and 25. Also, as illustrated in FIG. 28, arms 287 are concave inward and have sharp cutting edges 288 defined on sides thereof.

Relative motion between inner member 284 and outer member 286, which opens and closes arms 287, can be accomplished by a mechanism as disclosed in prior application Ser. No. 60/050,092 incorporated herein by reference. It should be appreciated, however, that the tissue collector 240 can include various handle structure for moving the inner member 284 and/or the outer member 286 relative to the other to move arms 287 between the fully open and fully closed positions. As an example, FIG. 26 illustrates tissue collector 240 with a U-shaped handle 289 having a distal leg 290 attached to inner member 284 and a proximal leg 291 attached to a proximal end of outer member 286. The handle 289 is preferably made of resilient or flexible material or a material having shape memory, such as spring material, to be normally disposed in a rest or relaxed position shown in FIG. 26. In the rest position for handle 289, a distal end of outer member 286 is disposed proximally of the distal end of inner member 284 such that the arms 287 are in the fully open position. Handle 289 is capable of being manually compressed causing the distal and proximal legs 290 and 291 to be moved closer to one another than they are in the rest position causing movement of inner member 284 proximally relative to outer member 286 and/or movement of outer member 286 distally relative to inner member 284 to move the arms 287 from the fully open position to the fully closed or a partially closed position. A longitudinal slot 292 is provided in outer member 286, and the distal leg 290 extends through the slot 292 to permit relative longitudinal movement of the inner and/or outer members 284 and 286. Upon release of a manual compressive or squeezing force on handle 289, the handle 289 returns to the rest position. It should be appreciated that the handle 289 can be provided with various locking mechanisms for locking the handle 289 in various compressed or squeezed positions.

In order to facilitate dissection or cutting with cutting edges 288, it is preferred that the inner member 284 be rotatable relative to the outer member 286 and that such rotation be capable of being imparted to the inner member 284 from a proximal end of the tissue collector 240. Accordingly, the inner member 284 can be rotatably mounted to the distal leg 290 of handle 289, and a proximal end 293 of inner member 284 extends proximally from the outer member 286 to be manually grasped and rotated as shown by the arrow in FIG. 26. Accordingly, the inner member 284 can be rotated about its central longitudinal axis relative to the outer member 286 for cutting of tissue by cutting edges 288. A valve 294 is disposed on the proximal end of inner member 284 for selectively opening and closing a lumen or passage therethrough extending longitudinally entirely through the tissue collector 240.

Figure 29:
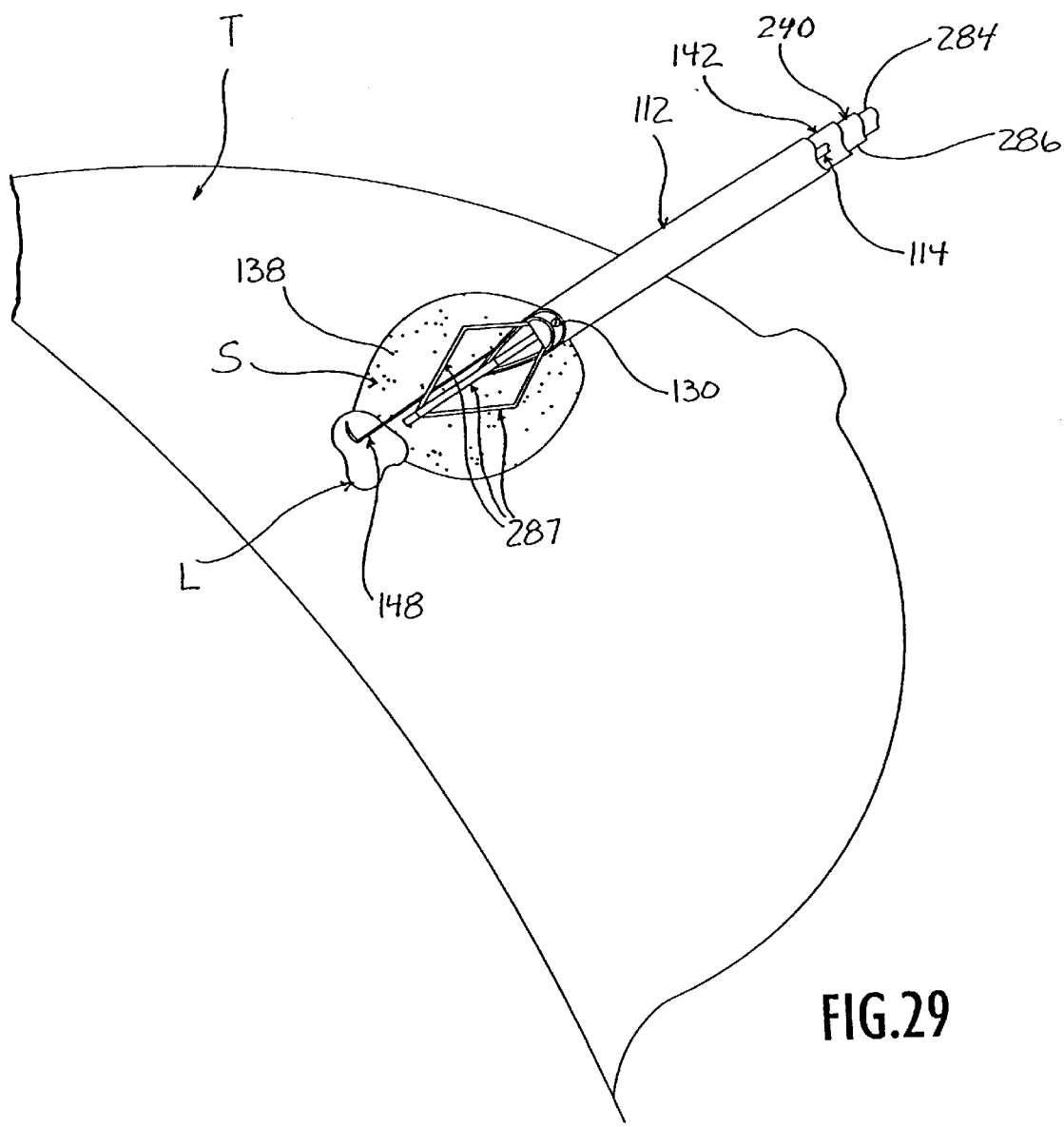
FIG. 29 illustrates insertion of the modified tissue collector through the anchoring device of the alternative instrument to position a distal end of the modified tissue collector in the space formed adjacent the lump.
Figure 30:
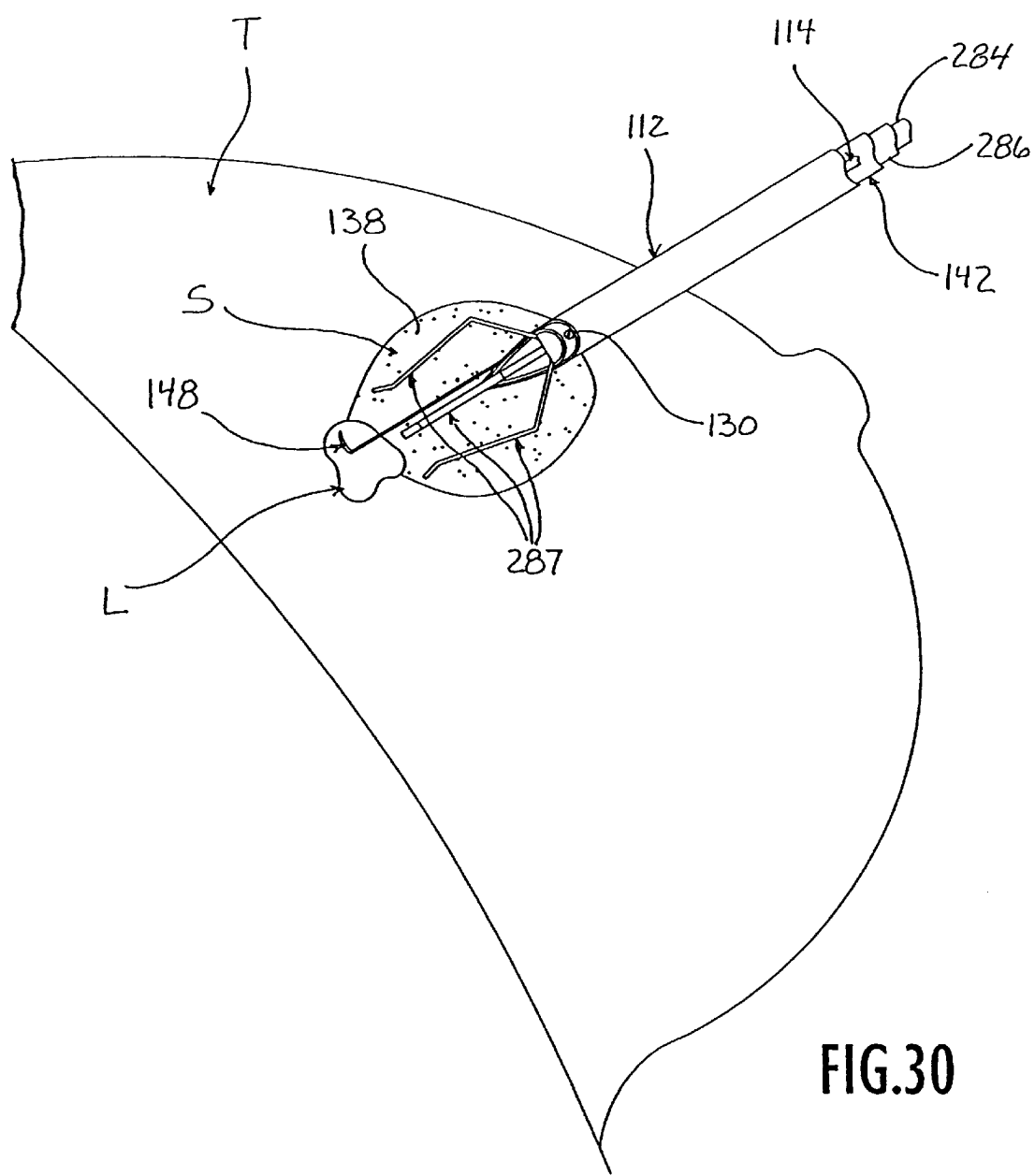
FIG. 30 depicts the modified tissue collector in the fully open position within the space.
Figure 31:
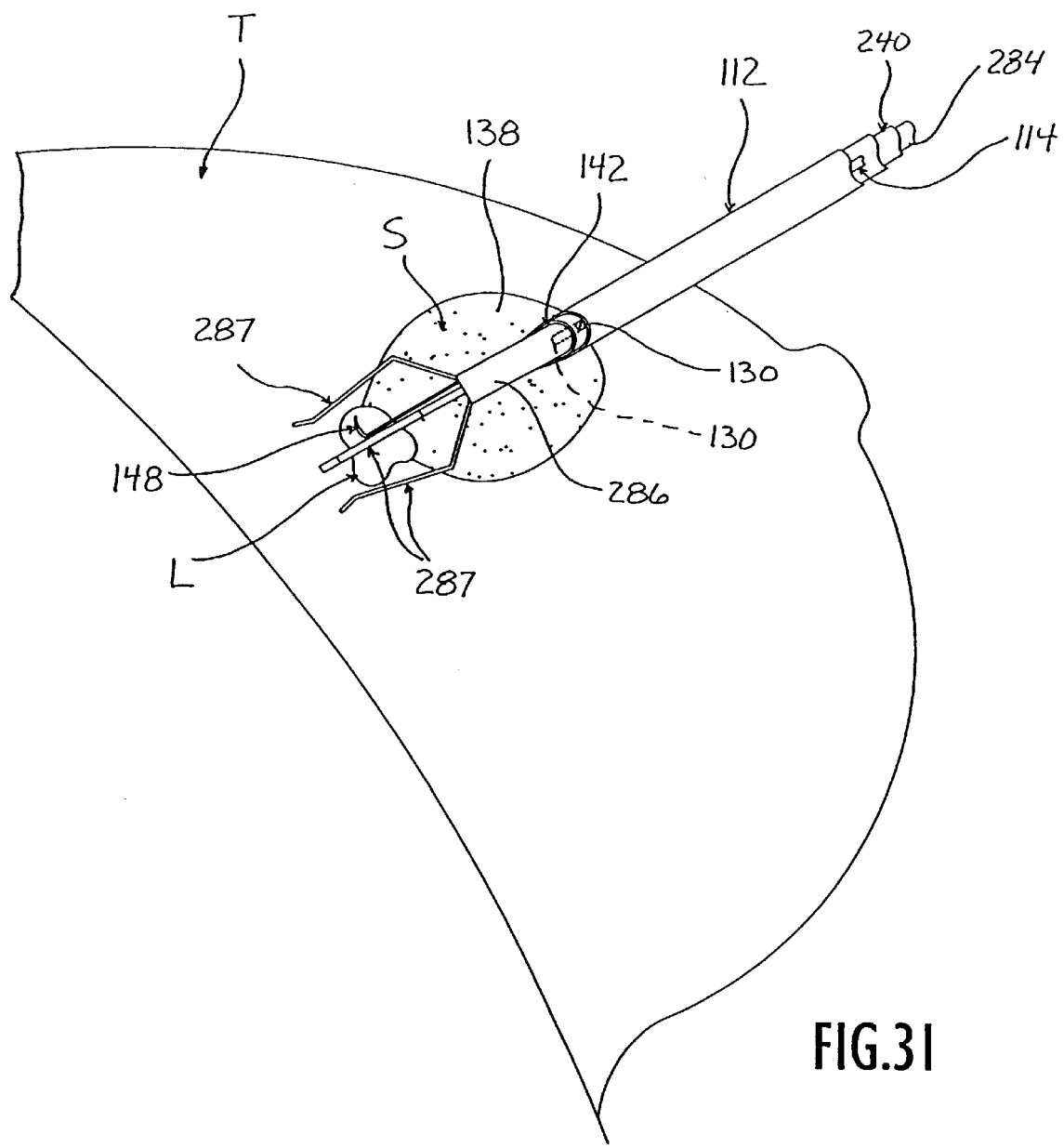
FIG. 31 illustrates the distal end of the modified tissue collector advanced into the breast tissue to be disposed around the lump.
Figure 32:
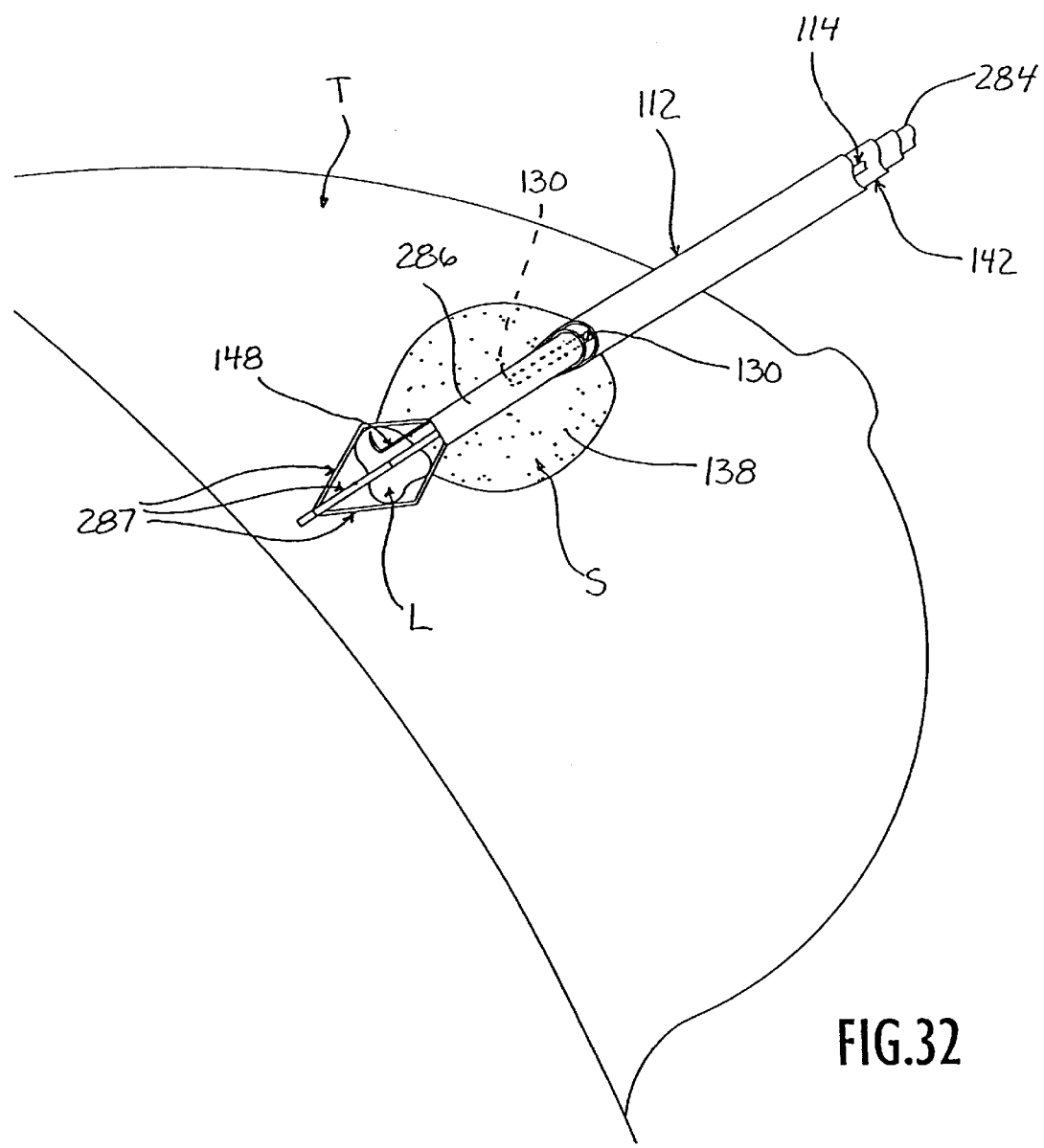
FIG. 32 illustrates the modified tissue collector in a closed position enclosing the lump for dissection and removal from the breast tissue.

FIGS. 29–32 illustrate a method of collecting tissue at an obstructed anatomical site according to the present invention wherein the tissue collected includes an entire lump. FIG. 29 illustrates space S created in breast tissue T adjacent lump L by fluidic material 138 injected through needle 112 and shows tong 148 of anchoring device 142 anchored in lump L in the manner described above. The anchoring device 142 illustrated in FIG. 29 has only one tong 148 for clarity of illustration. Tissue collector 240 is inserted through the anchoring device 287 to position arms 287 in space S. To facilitate insertion of tissue collector 240 through anchoring device 142, the arms 287 are moved to the fully closed position or to a partially closed position wherein the arms 287 are sufficiently closed to fit within the tubular body of anchoring device 142. Of course, the arms 287 can be designed to deflect, flex or "give" when inserted through the tubular body of anchoring device 142 such that the radial dimension of the arms 287 during insertion through anchoring device 142 can be larger than the radial dimension of the operating channel defined by the tubular body of the anchoring device 142. The tissue collector 240 is inserted through the anchoring device 142 to position arms 287 within space S externally of the tubular body of anchoring device 142 as shown in FIG. 29, and positioning of arms 287 in space S is confirmed visually with micro endoscope 114. The arms 287 disposed in space S are moved to the fully open position as shown in FIG. 30, the space S providing room for the spreading of arms 287 such that the cutting edges 288 do not contact and cut healthy breast tissue T. The arms 287 in the open position are advanced distally around lump L as shown in FIG. 31, which shows the endoscope 114 moved distally relative to the needle 112 to facilitate visual observation of the arms 287 around lump L. FIG. 32 illustrates the arms 287 moved to a partially closed position around lump L. In such partially closed position, a volume is defined between or is circumscribed by arms 287 corresponding substantially to the size and shape of lump L. Also, a small amount of surrounding tissue T can be contained in the volume defined by arms 287. In this state, the inner member 284, or both the inner member 284 and the outer member 286, can be rotated to cause cutting edges 288 to dissect tissue inside the defined volume from tissue outside or external of the defined volume, thusly separating or dissecting the tissue inside the defined volume from the remainder of tissue T.

Tissue collector 240 and anchoring device 142 can then be removed from breast tissue T with lump L contained between the arms 287 for retrieval of lump L external of the patient's body. Alternatively, the arms 287 can be opened sufficiently, while still in the breast tissue T, to permit tissue collector 240 to be removed from the patient's body without lump L. In the latter case, arms 287 are typically closed after releasing lump L and being backed away from lump L to facilitate withdrawal of the tissue collector 240 through the anchoring device 142. Also, in such a case, lump L can be removed from breast tissue T by anchoring device 142 since the tong 148 is attached to lump L, or the lump L can be removed by forceps or other appropriate tools. Tissue collector 240 allows lump L to be easily dissected from surrounding tissue and removed with minimal damage to surrounding tissue. This is particularly desirable when a lump or the like is removed from breast tissue because it minimizes or eliminates the need for any reconstructive or cosmetic surgery. The endoscope 114 is used to visualize the breast tissue T to confirm that all of the lump L is extracted. Once the tissue collector 240, the anchoring device 142 and the lump L have been withdrawn from breast tissue T, the needle 114 and the endoscope 115 are also withdrawn.

Depending on the nature of fluidic material 138 utilized to create space S, all or some of the fluidic material can remain in place to augment the breast by filling the void left by removal of lump L. Where all or substantially all of the fluidic material is aspirated from the breast tissue T following collection of lump L external of the patient's body, another fluid or other material can be injected through needle 112 or the anchoring device 142 to augment the breast.

It should be appreciated that tissue collector 240 can be used to collect a biopsy specimen of lump L by inserting arms 287 into lump L in a partially open position, closing arms 287 around a volume of lump L, less than its entire volume, and rotating at least the inner member 284 as described above to dissect the enclosed volume of lump L from the remainder thereof. Accordingly, in addition to lumpectomy procedures, the tissue collector 240 can be used as a specimen collector in biopsy procedures.

The methods of the present invention can be utilized for collecting specimens from any anatomical tissue and for removing lumps or other abnormal tissue, such as tumors, from any anatomical tissue and is not limited to soft tissue. For example, the methods of the present invention can be utilized to remove specimens and lumps such as tumors or the like from organs such as the lungs, liver, brain, kidney, gall bladder and bladder. Malignant and benign lumps or tumors can be removed or biopsied from any tissue or organ. Further, cysts, such as ovarian cysts, can be biopsied or removed using the methods of the present invention. The methods of the present invention can be practiced without the use of an anchoring device since direct visualization provided by the micro endoscope allows accurate positioning of the tissue collector to collect a tissue portion. The tissue collector can be any type of tissue collector that is insertable through the needle or through a second penetration or puncture. For example, the tissue collector can have a pair of opposing biopsy boxes mounted on a distal end thereof which close around tissue from which a specimen is to be collected. Also, the tissue collector can merely be a needle, cannula or the like which is inserted into the tissue from which a specimen is to be collected to cut a core-type sample.

The present invention facilitates minimally invasive tissue collection at an obstructed anatomical site by creating a space at the obstructed site adjacent tissue to be collected and thusly provides enhanced visualization and access of the tissue to be collected. The present invention allows tissue at the obstructed site to be dissected fluidically with minimal trauma and permits tissue to be collected to be dissected or separated from surrounding tissue. Where a space is created at an obstructed site in soft or resilient tissue, the tissue can merely decompress or spring back to fill in the space once the fluidic material is gone. The fluidic material does not have to be withdrawn from the tissue and can remain in the patient's body for natural absorption or dissipation or for permanent augmentation of the tissue. Accordingly, the need for reconstructive or cosmetic surgery is minimized or eliminated. Since the entire tissue collection procedure is visualized remotely with the endoscope, potentially harmful external imaging techniques need not be employed. The guide member is introduced in the anatomical tissue via a penetration or puncture that is preferably no larger than necessary to accommodate the external cross section of the guide member to minimize trauma and to allow the tissue collection procedures to be performed without general anesthesia and in non-hospital sites. Similarly, where instruments are introduced at the obstructed site through multiple punctures or penetrations, the multiple punctures or penetrations are preferably no larger than necessary to accommodate the instruments.

Inasmuch as the present invention is subject to many variations, modifications and changes in detail, it is intended that all subject matter discussed above or shown in the accompanying drawings be interpreted as illustrative only and not be construed as limiting the scope of the invention which is defined by the appended claims.

What is claimed is:

1. A method of collecting a tissue portion at an obstructed site within anatomical tissue comprising the steps of
    inserting a distal end of a guide member in the anatomical tissue;
    advancing the distal end of the guide member in the anatomical tissue to position the distal end of the guide member at the obstructed site adjacent the tissue portion;
    visualizing the obstructed site, from external of the anatomical tissue, with an endoscope disposed in the guide member;
    injecting a viscous, optically clear fluidic material at the obstructed site through a channel of the guide member to displace the anatomical tissue at the obstructed site and create a fluid filled space adjacent the tissue portion;
    introducing a distal end of a tissue collector in the space to access the tissue portion;
    dissecting the tissue portion from the anatomical tissue with the distal end of the tissue collector; and
    removing the tissue portion from the anatomical tissue.

2. A method of collecting a tissue portion as recited in claim 1 wherein said steps of inserting and advancing include penetrating the anatomical tissue with the distal end of the guide member.

3. A method of collecting a tissue portion as recited in claim 1 wherein said step of visualizing includes visualizing the obstructed site with an eyepiece of the endoscope.

4. A method of collecting a tissue portion as recited in claim 1 wherein said step of injecting includes injecting high density glucose at the obstructed site.

5. A method of collecting a tissue portion as recited in claim 4 wherein said step of injecting includes injecting Hyskon at the obstructed site.

6. A method of collecting a tissue portion as recited in claim 1 wherein said step of injecting includes fluidically dissecting the tissue portion from the anatomical tissue.

7. A method of collecting a tissue portion as recited in claim 1 wherein said step of removing includes removing the tissue portion with suction supplied through the tissue collector.

8. A method of collecting a tissue portion as recited in claim 1 wherein said step of dissecting includes dissecting a portion of a lump.

9. A method of collecting a tissue portion as recited in claim 1 wherein said step of dissecting includes dissecting an entire lump.

10. A method of collecting a specimen from a lump within anatomical tissue of a patient's body comprising the steps of
    inserting a distal end of a guide member in the anatomical tissue;
    advancing the distal end of the guide member in the anatomical tissue to position the distal end of the guide member adjacent the lump;
    visualizing positioning of the distal end of the guide member with an endoscope from external of the patient's body;

injecting a viscous, optically clear fluidic material in the anatomical tissue through the guide member from external of the patient's body;

displacing the anatomical tissue with the fluidic material to create a fluid filled space in the anatomical tissue adjacent the lump;

visualizing the lump with the endoscope;

introducing a distal end of a tissue collector in the space to access the lump;

collecting a specimen of the lump with the distal end of the tissue collector; and removing the specimen from the patient's body.

11. A method of collecting a specimen as recited in claim 10 wherein said steps of inserting and advancing include inserting and advancing the guide member in the anatomical tissue with the endoscope disposed in the guide member.

12. A method of collecting a specimen as recited in claim 10 wherein said step of injecting includes injecting Hyskon in the anatomical tissue.

13. A method of collecting a specimen as recited in claim 10 wherein said step of displacing includes fluidically dissecting the lump from the anatomical tissue.

14. A method of collecting a specimen as recited in claim 13 wherein said step of injecting includes injecting the fluidic material between the lump and the anatomical tissue.

15. A method of collecting a specimen as recited in claim 10 wherein said step of displacing includes exposing the lump in the space.

16. A method of collecting a specimen as recited in claim 10 wherein said step of introducing includes introducing the tissue collector through the guide member.

17. A method of collecting a specimen as recited in claim 10 wherein said step of collecting includes dissecting a portion of the lump from the remainder thereof.

18. A method of collecting a specimen as recited in claim 10 and further including, prior to said step of collecting, the steps of introducing a distal end of an anchoring device in the space and engaging the lump with the distal end of the anchoring device.

19. A method of collecting a specimen as recited in claim 18 wherein said step of introducing the distal end of the anchoring device includes introducing the anchoring device through the guide member.

20. A method of collecting a specimen as recited in claim 19 wherein said step of introducing the distal end of the tissue collector includes introducing the tissue collector through a channel of the anchoring device.

21. A method of removing a lump from within anatomical tissue of a patient's body comprising the steps of inserting a distal end of a guide member in the anatomical tissue;

advancing the distal end of the guide member in the anatomical tissue to position the distal end of the guide member adjacent the lump;

injecting a viscous, optically clear fluidic material in the anatomical tissue through the guide member from external of the patient's body;

displacing the anatomical tissue with the fluidic material to create a fluid filled space in the anatomical tissue adjacent the lump;

introducing a distal end of a tissue collector in the space from external of the patient's body;

dissecting the lump from the anatomical tissue with the distal end of the tissue collector;

visualizing dissection of the lump with an endoscope from external of the patient's body; and removing the lump from the patient's body.

22. A method of removing a lump as recited in claim 21 wherein said steps of inserting and advancing include inserting and advancing the guide member in the anatomical tissue with the endoscope disposed in the guide member.

23. A method of removing a lump as recited in claim 21 wherein said step of injecting includes injecting Hyskon in the anatomical tissue.

24. A method of removing a lump as recited in claim 21 wherein said step of displacing includes fluidically dissecting the lump from the anatomical tissue.

25. A method of removing a lump as recited in claim 24 wherein said step of injecting includes injecting the fluidic material between the lump and the anatomical tissue.

26. A method of removing a lump as recited in claim 21 wherein said step of displacing includes expo sing the lump in the space and further including the step of visualizing the thusly exposed lump with the endoscope.

27. A method of removing a lump as recited in claim 21 wherein said step of introducing the distal end of the tissue collector includes introducing the tissue collector through the guide member.

28. A method of removing a lump as recited in claim 21 wherein said step of dissecting includes dissecting the lump and a portion of surrounding anatomical tissue from the remainder of the anatomical tissue.

29. A method of removing a lump as recited in claim 21 wherein said step of dissecting includes containing the lump within the distal end of the tissue collector.

30. A method of removing a lump as recited in claim 29 wherein said step of removing includes withdrawing the distal end of the tissue collector from the patient's body with the lump contained therein.

31. A method of removing a lump as recited in claim 21 and further including, prior to said step of dissecting, the steps of introducing a distal end of an anchoring device in the space from external of the patient's body and engaging the lump with the distal end of the anchoring device.

32. A method of removing a lump as recited in claim 31 wherein said step of introducing the distal end of the anchoring device includes introducing the anchoring device through the guide member.

33. A method of removing a lump as recited in claim 32 wherein said step of introducing the distal end of the tissue collector includes introducing the tissue collector through a channel of the anchoring device.

* * * * *